United States Patent [19]

Ito et al.

[11] Patent Number: 5,369,600
[45] Date of Patent: Nov. 29, 1994

[54] APPARATUS FOR MEASURING GAS DENSITY AND SUGAR CONTENT OF A BEVERAGE WITHIN A SEALED CONTAINER AND METHOD OF MEASURING THE SAME

[75] Inventors: Yasushi Ito; Shogo Yamaguchi; Hironobu Fujikake; Sadahiro Abe; Masaru Nishimura; Noriaki Matsumura; Takashi Tanaka, all of Nagoya, Japan

[73] Assignees: Mitsubishi Jukogyo Kabushiki Kaisha, Tokyo; Churyo Engineering Kabushiki Kaisha, Nagoya, both of Japan

[21] Appl. No.: 996,167

[22] Filed: Dec. 23, 1992

[30] Foreign Application Priority Data

Dec. 24, 1991 [JP] Japan .................. 3-341294
Dec. 24, 1991 [JP] Japan .................. 3-341295
Mar. 24, 1992 [JP] Japan .................. 4-066137
Sep. 17, 1992 [JP] Japan .................. 4-247769

[51] Int. Cl.$^5$ .................. G01L 7/00; G01N 7/00
[52] U.S. Cl. .................. 364/556; 364/550; 73/19.03; 73/19.06
[58] Field of Search .................. 364/556, 550, 499, 558, 364/579; 73/19.01, 19.03, 19.06

[56] References Cited

U.S. PATENT DOCUMENTS 4,745,794  5/1988  Steichen et al. .................. 73/19.03
4,763,525  8/1988  Cobb .................. 73/19.03 X
5,220,513  6/1993  Seiden et al. .................. 364/499 X Primary Examiner—Jack B. Harvey
Assistant Examiner—Edward Pipala
Attorney, Agent, or Firm—Jacobson, Price, Holman & Stern

[57] ABSTRACT

An apparatus and method in which the lateral surface of a sealed container (11) containing a beverage liquid (12) is pressed (21, 22) for deformation to measure the internal pressure (P) of the container, and displacement caused by the pressure and the load (F, 31) applied by the pressure is detected (35) so that the gas density of the beverage liquid may be evaluated from these values. An ultrasonic pressure wave is applied (111) to the sealed container to measure the sugar content of the beverage from the propagation velocity of the pressure wave received by an ultrasonic receiver (112), container surface temperature and the ambient temperature resulting from sensors (121, 122) and a calculation unit (50). For simultaneously measuring the gas density and the sugar content a gas density measuring unit (220, 230, 240) and a sugar content measuring unit (290) are provided. In addition, for shaking the content of a sealed container in which the container (500) is placed in a water tank (503), an ultrasonic wave is generated from an ultrasonic shaker (501) provided at the bottom of the water tank to agitate the content of the container for uniformity.

18 Claims, 18 Drawing Sheets

F I G. I

F I G. 4
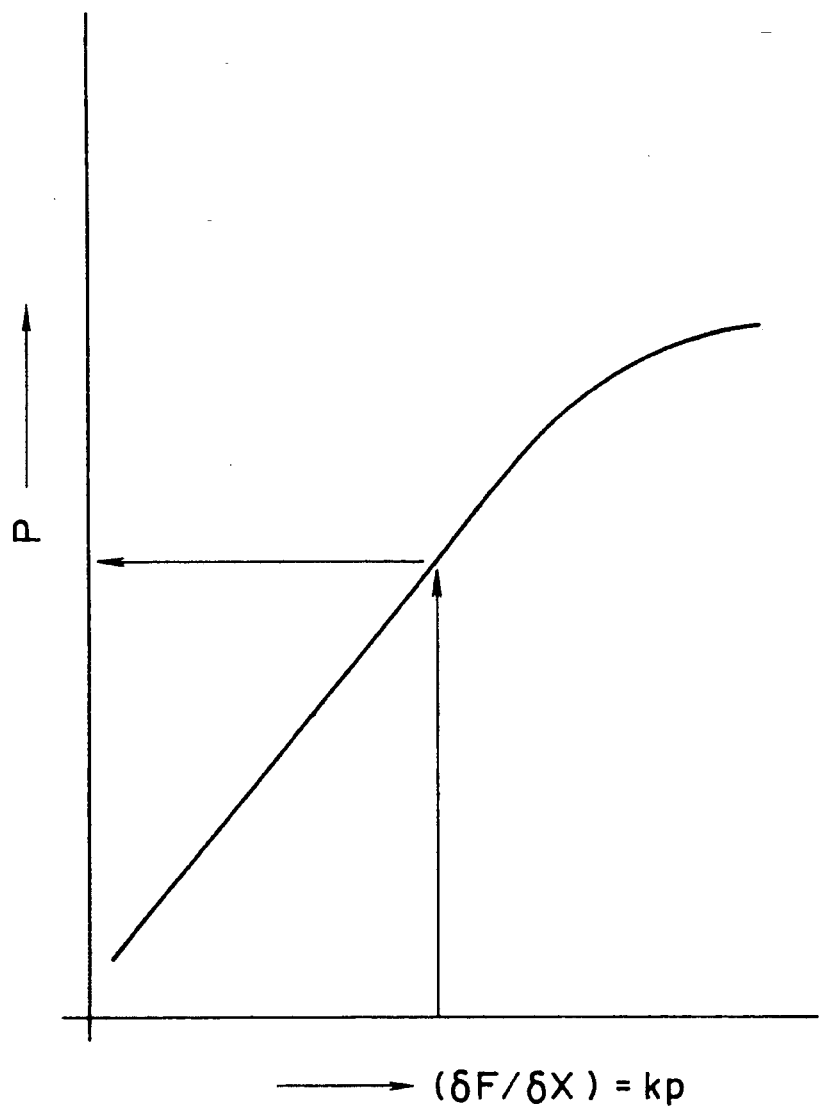

F I G. 11
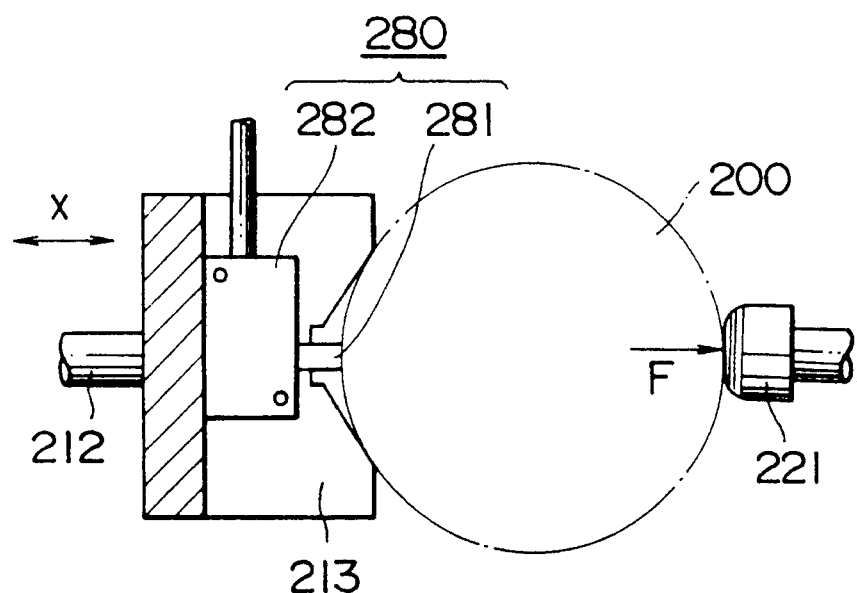
F I G. 12A
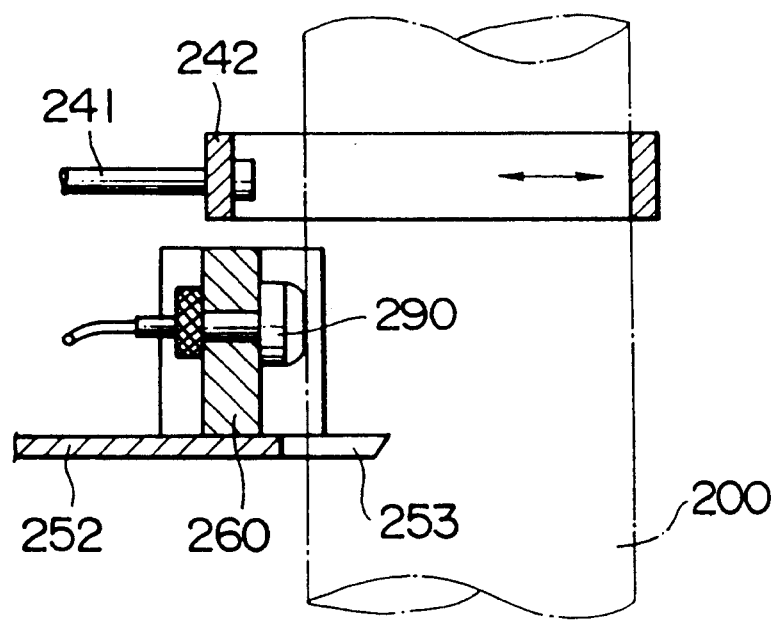

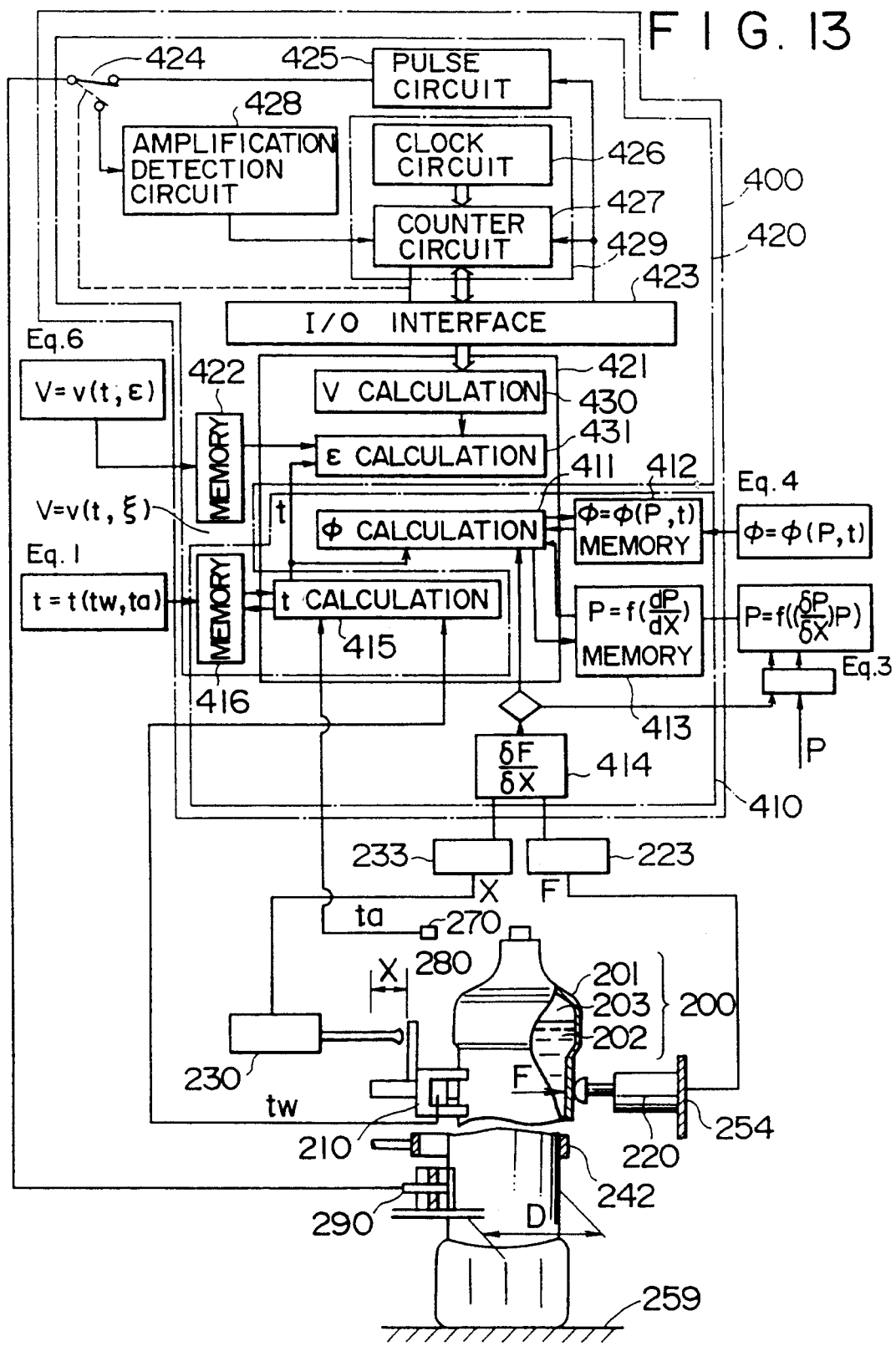

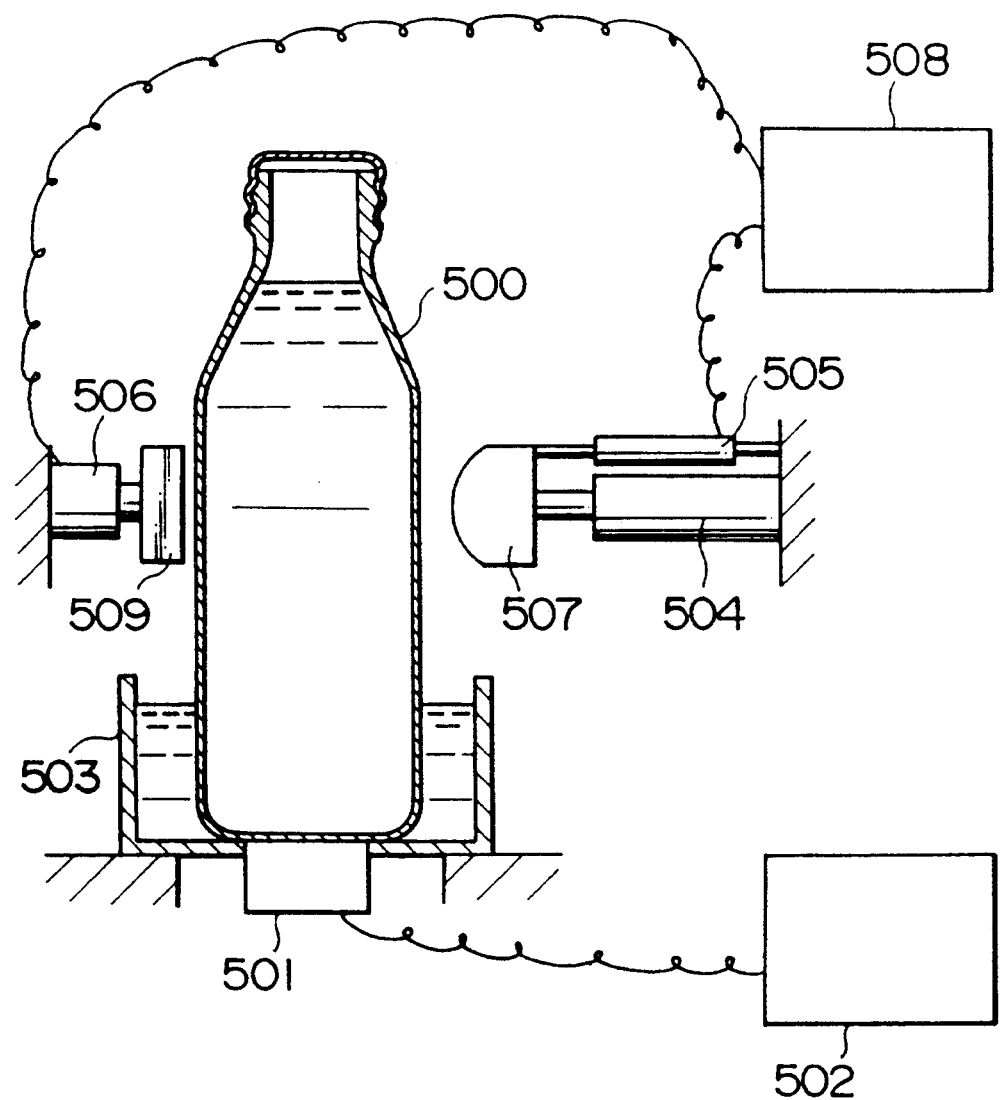
F I G. 15

APPARATUS FOR MEASURING GAS DENSITY AND SUGAR CONTENT OF A BEVERAGE WITHIN A SEALED CONTAINER AND METHOD OF MEASURING THE SAME

BACKGROUND OF THE INVENTION

Field of the Invention

The present invention relates to an apparatus for measuring the gas density and sugar content of a beverage within a sealed container and a method of measuring the same.

More specifically, the present invention relates to an apparatus for measuring the gas density in a beverage within a sealed container and a method of measuring the same, an apparatus for measuring the sugar content of a beverage within a sealed container and a method of measuring the same, an apparatus for and method of simultaneously measuring the gas density and sugar content of a beverage within a sealed container, and a shaker used for a nondestructive inspection apparatus for shaking and agitating the content of a container containing a water-soluble gas and having an elastically deformable barrel portion, such as a can or sealed plastic container prior to inspecting its internal pressure, sugar content or the like.

Description of the Related Art

Conventionally, as a sealed container for a beverage a thin wall container made of a metal or a plastic material has been used.

It is important to control the quality of a beverage, such as a carbonated beverage, beer or the like, after it is automatically filled using a filling machine. For such beverages to which pressure is applied when filled, a sampling test has been carried out on their gas density characteristics.

A conventional example of this method is described with reference to FIG. 23, in which reference numeral 710 denotes a measuring stand, 711 a base for the measuring stand 710, 712 a lateral guide bar erected on the base 711, 714 a sliding stand slidably supported by each guide bar 712, 713 a grip mounted at opposite ends of each sliding stand 714, 700 a pressure measuring head supported by the sliding stand 714, 701 a piercing needle, 702 a main body, 703 a passageway for introducing pressure which is formed within the main body 702, 704 an on-off valve, 705 a pressure gauge, 720 a sealed container, 721 a cap for the sealed container 720, 730 a matter filled in the sealed container 720, 731 a portion filled with the beverage and 732 a portion filled with the gas (gas phase portion).

When the gas density in the sealed container 720 is measured, the container 720 is placed on the base 711 and, subsequently, the on-off valve 704 is closed. Then, the sliding stand 714 and the pressure measuring head 700 are lowered to pierce through the cap 721 of the sealed container 720 by means of the piercing needle 701. The lower end portion of the piercing needle 701 enters into the sealed container 720 to introduce the gas 730 in the sealed container 720 from the piercing needle 701 through the passageway 703 to the pressure gauge 705 to measure the internal pressure p of the container 720. Subsequently, the cap 721 is removed to measure the temperature t of the beverage liquid 731 within the container 720 by means of a thermometer (not shown). The gas density is evaluated from the internal pressure p of the container 720, the temperature t of the beverage liquid 731, and the known solubility characteristic (see FIG. 5).

Next, a conventional example of the method of measuring the sugar content of a beverage within the sealed container is described.

When the sugar content of the beverage 731 of the sealed container 720 is measured, first, the container 720 is opened, and then a proper amount of beverage 731 is extracted as a sample to make measurements on. Subsequently, the extracted sample is placed on the measuring portion of a sugar meter using an optical refractometer. The sample is left as it is until it reaches a predetermined temperature, and its sugar content is calculated from the measured refraction index and the temperature. Finally, the calculated sugar content value is recorded.

When the sampling test is carried out to find out changes in the properties and specific characteristics of the content of the filled foodstuff or beverage and the extent of such changes without destroying the container, it is necessary to shake the sealed container, agitate its content well enough and make the content uniform so that the measuring accuracy of measurement may be improved.

Further, in the case of a gas-filled beverage, it is also necessary to increase the measuring accuracy by shaking the container and agitating it well enough to bring the solubility of the gas in the water into an equilibrium state.

Here, conventionally, prior to carrying out the foregoing test, after the sealed container filled with the solution is manually shaken and fully agitated, it is mounted on the non-destructive test machine for measurement.

Also for a non-destructive testing machine for inspecting all products produced in sealed containers, an apparatus has already been proposed in which the sealed container is subjected to vibrations produced by a conveyer to agitate and mix the solution and the gas within the container, and, with the content being kept in a resonant state, every product is passed through supersoft X-rays to inspect for any abnormalities and their extent (See Japanese Patent Provisional Publication (Kokai) No. 2-309230, if necessary).

SUMMARY OF THE INVENTION

In one aspect of the present invention, the method and apparatus each aims at solving the following problems inherent to the foregoing conventional arrangements.

(1) Because of the destructive test, it is impossible to incorporate them into the production line.

(2) Because they are destructive tests, containers have to be discarded after inspection, and a loss of products results. It is impossible to inspect all products produced.

(3) The dead volume of the measuring system added to measure the pressure is large as compared with that of the gas filling portion (gas phase portion) 732 within the container 720. This leads to a large error in the pressure measurement, making it impossible to achieve a precise density measurement.

A first aspect of the present invention has been proposed in view of those problems. Its object is to provide an apparatus for and a method of measuring gas density in the beverage within the sealed container which allows the gas density of the beverage to be measured in a non-destructive, precise and efficient manner.

In order to achieve this end, in the first aspect of the present invention, the apparatus for measuring the gas density has the following arrangement.

That is, the apparatus according to the first aspect of the present invention comprises a pressing means 20 for pressing the lateral surface of the sealed container 10 with varying loads F, a displacement measuring means 35 for elastically deforming the container 10 by the pressing means 20 to measure the displacement X of the pressing means 20 when the internal pressure p of the container is changed, a load measuring means 30 for measuring the load F applied to the pressing means 20, a means 40 for calculating the rigidity of the container for calculating the container rigidity $((\alpha F/\alpha X)_{p=p})$ against the internal pressure P from the results measured by those means, a means 41 for non-destructively measuring the pressure P within the container by specifying the gradient characteristic $(P=P(\alpha F/\alpha X)_p)$ from the result based on the container rigidity $(\alpha F/\alpha X)_{p=p}$ against the known container internal pressure P from this measurement made by those means and a means for calculating the solubility characteristic for calculating the solubility $\phi$ of the gas within the beverage from the solubility characteristic $\phi(P, T)$ determined according to the kinds of the gas and the beverage.

Further, according to the first aspect of the present invention, the method of measuring the gas density within the beverage comprises the following steps. That is, changing the load F by means of the pressing means 20, the lateral surface of the container 10 is pressed to elastically deform the container 10. The displacement X of the pressing means 20 when the internal pressure P is changed is measured by the displacement measuring means 35, while the load F applied to the pressing means 20 is simultaneously measured by the load measuring means 30. Those measured results are fed to the rigidity calculating means 40 to calculate the container rigidity $(\alpha F/\alpha X)_p$ against the internal pressure. The calculated result is fed to the non-destructive measurement means 41 to specify the gradient characteristic $(P=f(\alpha F/\alpha X)_p)$ based on the known container rigidity $(\alpha F/\alpha X)_p$ relative to the known internal pressure P so as to non-destructively measure the internal pressure P. These internal pressure value and surface temperature value from the temperature measuring means 42, and the solubility characteristic $\phi(P, T)$ which is determined depending on the kind of the gas and beverage are fed to the solubility characteristic calculating means 50 to calculate the solubility $\phi$ of the gas in the beverage.

The function of the foregoing method and apparatus is as follows. When the gas density within the beverage is measured, as described above, changing the load F by the pressing means 20, the lateral surface of the container 10 is pressed to elastically deform the container 10. The displacement X of the pressing means 20 when the internal pressure p is changed is measured by the displacement measuring means 35 while, at the same time, the load F applied to the pressing means 20 is measured by the load measuring means 30. These measured results are fed to the container rigidity calculating means 40 to calculate the container rigidity $(\alpha F/\alpha X)_{p=p}$ relative to the internal pressure. This calculated result is fed to the non-destructive measuring means 41 to specify the gradient characteristic $P=P(\alpha F/\alpha X)_{p=p}$ relative to the known internal pressure p to non-destructively measure the internal pressure p. Next, this measured result of internal pressure, surface temperature value from the temperature measuring means 42, and the solubility characteristic $\phi(P, T)$ determined depending on the kind of the gas and beverage are fed to the solubility characteristic calculating means 50 so as to calculate the solubility $\phi$ of the gas in the beverage (that is, the gas density of the beverage within the sealed container 10 is measured.)

In consequence, according to the apparatus and method according to the first aspect of the present invention, the gas density prevailing within the beverage can precisely and efficiently be measured in a non-destructive manner.

The apparatus and method of measuring the sugar content according to a second aspect of the present invention overcomes the following problems inherent in the foregoing conventional method.

(1) In order to measure the sugar content of the beverage, it is necessary to open a sealed container to extract a proper amount of beverage as a measuring sample for measurement. This requires a labor-consuming batch technique leading to an increase in the costs of the measurement.

(2) From the sanitary point of view, it is necessary to discard the sealed containers and their content after measurement. This causes production losses while, at the same time, making it impossible to carry out the inspection on all products, although such testing on all products is certainly desirable.

An object of the second aspect of the present invention is provide an apparatus for and a method of measuring the sugar content of a beverage within a sealed container which makes a reduction in the costs of measurement possible and prevents production losses while allowing all products to be tested.

In order to achieve the foregoing end, the apparatus according to the second aspect of the present invention comprises a calculation control means; a pulser for converting a measurement start signal from the calculation control means into a high voltage pulse; an ultrasonic sensor having a wave sender portion for converting the high voltage pulse from the pulser into a pressure wave of a frequency in the ultrasonic range to radiate it into the beverage within the sealed container and a wave receiver portion for receiving this pressure wave; an amplifier for amplifying an output signal from the wave receiving portion; a comparator for comparing the output signal from the amplifier with a preset value; an ultrasonic timing means which starts to time with the measurement start signal from the calculation control means and ends upon receipt of the output signal from the comparator; a container surface temperature sensor for measuring the surface temperature of the sealed container; an ambient temperature sensor for measuring the temperature surrounding the sealed container; a pressure contact means for bringing the ultrasonic sensor and the container surface temperature sensor into press-contact with the sealed container; said calculation control means, after the container surface temperature sensor of the ultrasonic sensor is made to press-contact the sealed container, calculating the temperature of the beverage with the surface temperature measurement signal and the ambient temperature measurement signal from each sensor while calculating the propagating velocity of the pressure wave according to the timing signal from the ultrasonic timing means and the propagation distance of the pressure wave within the beverage to further calculate the sugar content of the beverage according to this propagation distance and the foregoing calculated distance; and a sugar content display means for displaying or recording the result calculated by the calculation control means.

Further, the method of measuring the sugar content according to the second aspect of the present invention is as follows. That is, the ultrasonic sensor and the container surface temperature sensor are made to press-contact the sealed container by means of the pressing means. Next, after the measurement start signal pulse from the calculation control means is converted into a high voltage pulse, it is converted into the pressure wave having an ultrasonic frequency in the ultrasonic range by means of the wave sender portion of the ultrasonic sensor. The pressure wave is then radiated into the beverage within the sealed container.

Further, after this pressure wave is received by the wave receiver portion of the ultrasonic sensor and the output signal from the wave receiver portion is amplified by the amplifier, it is compared with a preset value by means of the comparator. Next, the ultrasonic timing means starts to time according to the measurement start signal pulse from the calculation control means while the timing is completed according to the output signal from the comparator. In addition, the surface temperature of the sealed container is measured by the container surface temperature sensor, and the temperature surrounding the sealed container is measured by the ambient temperature sensor. The temperature of the beverage within the sealed container is calculated by the calculation control means according to the surface temperature measurement signal from the container surface temperature sensor and the ambient temperature measurement signal from the ambient temperature sensor, while the propagation velocity of the pressure wave is calculated according to the timing signal from the ultrasonic timing means and the propagation distance of the pressure wave within the beverage, and, further, the sugar content of the beverage is calculated according to this propagation velocity and the foregoing calculated beverage temperature so as to be displayed or recorded by the sugar content display means.

The function of the foregoing apparatus and method according to the second aspect of the present invention is as follows.

That is, after the ultrasonic sensor and the container surface temperature sensor are caused to press-contact onto the outer surface of the sealed container, the calculation control means calculates the beverage temperature according to the surface temperature measurement signal and the ambient temperature measurement signal from each temperature sensor. Then, the propagation velocity of the pressure wave is calculated according to the timing signal from the ultrasonic timing means and the propagation distance of the pressure wave (acoustic wave) within the beverage. Further, the sugar content of the beverage is calculated according to this propagation velocity and the foregoing calculated beverage temperature, and the result is displayed or recorded by the sugar content display means.

Therefore, according to the apparatus and method of the second aspect of the present invention, unlike conventional methods, it is not necessary to open the sealed container to extract a proper amount of the beverage as a sample to be measured, and it is possible to measure the sugar content within the production line to thereby reduce the costs of measurement.

Further, it is also not necessary to open the sealed container, as described above, to extract some amount of the beverage as a sample to make measurement on, which lends itself to eliminating production losses while allowing every product produced to be inspected.

Next, a third aspect of the present invention provides an apparatus and method of simultaneously measuring the gas density and the sugar content of the beverage which may improve the inspecting efficiency and make it possible to inspect all products produced, when the gas density and sugar content need to be measured.

In order to achieve this end, the apparatus according to the third aspect of the present invention for simultaneous measurement of the sugar content and gas density of a beverage in a sealed container comprises a means for measuring the gas density of the beverage within a sealed container; a means for measuring the sugar content of the beverage; and a control means for displaying and recording the measured values of the gas density $\phi$ and the sugar content $\xi$, time adjustment, and the container number, and for controlling the movement and pressing force of the pressing means.

The foregoing gas density measuring means and sugar content measuring means are arranged as follows.

That is, the foregoing gas density measuring means comprises a container stand 250 of box shape for placing a sealed container 200 containing a beverage 202 and a gas 203 within a container body 201 under internal pressure P, a surface temperature means 280 for detecting the surface temperature $t_w$ of the sealed container 200, an ambient temperature means 270 for detecting the ambient temperature $t_a$ of the sealed container 200, a load measuring means 220 fixed to a part of the container stand 250, a pressing means 210 for forcing the sealed container 200 against the load measuring means 220, a displacement measuring means 230 for measuring the displacement of the pressing means 210, a container rigidity calculation means 414 for calculating the container rigidity $k_p = (\alpha F / \alpha X)_p$ from the pressing force F of the pressing means 210 and the displacement X of the displacement measuring means 230, a temperature characteristic storage means 416 for storing a relationship $t = t(t_w, t_a)$ among the container surface temperature $t_w$, container's ambient temperature $t_a$ and the liquid temperature t within the container, a container rigidity calculation storage means 413 for storing a relationship $P = P(k_p)$ between the internal pressure P of the container and the container rigidity $k_p$, a gas-liquid equilibrium characteristic storage means 412 for storing the gas-liquid equilibrium characteristic $\phi = \phi(P, t)$ which depends on the kind of beverage 202, the internal pressure P of the container, and the liquid temperature t inside the container, a temperature characteristic calculation means 415 for calculating the liquid temperature t within the container from a relationship $t = t(t_w, t_a)$ among the container surface temperature $t_w$, the container's ambient temperature $t_a$ and the liquid temperature t within the container, and a gas-liquid equilibrium density calculation means 411 for, after the internal pressure p of the container is calculated from the container rigidity $k_p$ outputted by the container rigidity calculation means 414, calculating the gas density $\phi$ in the beverage 202 from the internal pressure p and the liquid temperature t within the container which is obtained from the temperature characteristic calculation means 415 and the gas-liquid equilibrium characteristic $\phi = \phi(P, t)$ when the liquid and the gas are in an equilibrium state.

In addition, the foregoing sugar content measuring means comprises a pressing means 240 for forcing the sealed container 200 placed on the fixed container stand 250 against the ultrasonic vibrator 290; an ultrasonic shaker means 425 for driving the ultrasonic vibrator 290 by a single pulse; an ultrasonic vibrator 290 for shaking the sealed container 200 by the ultrasonic shaker means 425 to induce an elastic wave in the range of the ultrasonic wave; an ultrasonic wave detecting means 428 for amplifying the electrical output from the ultrasonic vibrator 290 to detect an envelope thereof; a means 430 for calculating the propagation velocity V of the ultrasonic wave within the beverage 202 according to the outputs from the ultrasonic shaker 425 and the ultrasonic detector 428; a sound velocity characteristic storage means 422 for storing the sound velocity characteristic relationship $V=v(t, \xi)$ among the propagation velocity V of the ultrasonic wave, liquid temperature t within the container and the sugar content $\xi$; and a sugar content calculation means 431 for calculating the sugar content $\xi$ of the beverage 202 from the propagation velocity V of the ultrasonic wave, liquid temperature t within the container and the foregoing relationship $V=v(t, \xi)$.

In the above-described apparatus for simultaneous measurement of the sugar content and gas density, a pair of ultrasonic vibrators can be disposed so that they face each other with the sealed container on which measurements are carried out being placed therebetween. In such a case, one ultrasonic vibrator can be mounted on the pressing means 240.

That is, the sugar content measuring means may comprise a pair of ultrasonic vibrators; a press-contact means for pressing the sealed container at two opposite positions thereon as the container is placed on the container stand of box shape against the two ultrasonic vibrators; an ultrasonic shaker means for driving the ultrasonic vibrators with a single pulse; the two ultrasonic vibrators being energized by the ultrasonic shaker means for inducing an ultrasonic elastic wave motion in the sealed container; an ultrasonic wave detecting means for amplifying an electrical output from the ultrasonic vibrators and detecting an envelope thereof; a propagation velocity calculation means for calculating the propagation velocity V of the ultrasonic wave within the beverage liquid based on the outputs from the ultrasonic shaker means and the ultrasonic wave detecting means; a sound velocity characteristic storage means for storing a relationship $V=v(t, \xi)$ between the propagation velocity V of the ultrasonic wave, the liquid temperature t in the container and the sugar content $\xi$; and a sugar content calculation means for calculating the sugar content of the beverage liquid from the propagation velocity V of the ultrasonic wave, the liquid temperature t in the container and the foregoing relationship $V=v(t, \xi)$.

Furthermore, the measuring method according to the third aspect of the invention is as follows.

The apparatus used herein for simultaneously measuring the gas density and sugar content comprises a means for measuring the gas density of the beverage within the sealed container; a means for measuring the sugar content of the beverage; and a control means for carrying out such functions as displaying and recording the measured values of the gas density $\phi$ and the sugar content $\xi$, the adjustment time and the container number, and controlling the movement and pressing force of the pressing means and the movement of the press-contact means.

Using this apparatus, first, the sealed container 200 containing the beverage 202 and the gas 203 within the container body 201 under the internal pressure P is placed upright on the container stand 250 of box shape. Then, the surface temperature $t_w$ of the sealed container 200 is measured by means of the surface temperature detecting means 280, and the ambient temperature $t_a$ of the sealed container 200 is measured by means of the ambient temperature detecting means 270. In addition, the sealed container 200 is forced against the load measuring means 220 fixed to a part of the container stand 250 by means of the pressing means 210, and the displacement of the pressing means 210 is measured by means of the displacement measuring means 230. Next, the container rigidity $k_p=(\alpha F/\alpha X)_p$ is calculated from the pressing force F of the pressing means 210 and the displacement X obtained for the displacement measuring means 230 by means of the container rigidity calculation means 414. Further, the liquid temperature t within the container is calculated from the relationship $t=t(t_w, t_a)$ among the container surface temperature $t_w$, the container ambient temperature $t_a$ and the liquid temperature t within the container, which is stored in the temperature characteristic storage means 416, by means of the temperature characteristic calculation means 415, and the internal pressure P of the container p is calculated from the relationship $P=p(k_p)$ between the internal pressure p of the container and the container rigidity $k_p$, which is stored within the container rigidity storage means 413, by means of the container rigidity calculation means. Thereafter, the gas density $\phi$ prevailing within the beverage 202 when the liquid and the gas are in an equilibrium state is calculated from this result and the gas-liquid equilibrium density characteristic $\phi=\phi(P, t)$ which depends on the kind of the beverage 202, the internal pressure P of the container and the liquid temperature t in the container, which are stored within the gas-liquid equilibrium characteristic storage means 412, by means of the gas-liquid equilibrium density calculation means 411.

In addition, the sealed container 200 placed on the container stand 250 of box shape is forced against the ultrasonic vibrator 290 by means of the pressure-contact means 240. Next, the ultrasonic vibrator 290 is driven with a single pulse by the ultrasonic shaker 425 to induce an ultrasonic elastic wave to the sealed container 200, and the electrical output from the ultrasonic vibrator 290 is amplified by means of the ultrasonic wave detecting means 428 for detection of an envelope of the output. From the outputs from the ultrasonic shaker 425 and the ultrasonic wave detecting means 428, the propagation velocity V of the ultrasonic wave within the beverage 202 is calculated by means of the propagation velocity calculation means 430. Then, the sugar content $\xi$ is calculated from the relationship $V=v(t, \xi)$ among the ultrasonic propagation velocity V, liquid temperature t within the container and the sugar content $\xi$, which are stored in the sound velocity characteristic storage means 422, by means of the sugar content calculation means 431.

In the above-described method, it is also possible to press the sealed container at two opposite positions thereon using a pair of ultrasonic vibrators with a press-contact means as the sealed container is placed on the container stand, drive at least one of the ultrasonic vibrators by a single pulse from an ultrasonic shaker means to induce an ultrasonic elastic wave to the sealed container, and amplify an electrical output from at least one of the ultrasonic vibrators and detect an envelope thereof.

The function of the apparatus and method according to the third aspect of the present invention is as follows. That is, by utilizing the fact that the container rigidity is determined by the internal pressure of the sealed container, the gas density $\phi$, within the beverage is measured. In addition, in order to measure the sugar content $\xi$ of the beverage, the propagation velocity characteristic of ultrasonic waves is utilized. In consequence, without having to open the sealed container, the measurement of the gas density within the beverage and the measurement of the sugar content of the beverage may be simultaneously and precisely achieved with the result that an improvement in the inspection efficiency and the inspection of all products produced are simultaneously achieved.

A shaker apparatus according to a fourth aspect of the present invention intended to solve the following problems which occur when the content of the sealed container is shaken and agitated.

(1) When the sealed container is manually shaken and agitated, it is difficult to make the shaking conditions uniform. As a result, the measuring accuracy of the saturated pressure within the container is low, and the determination of the gas density within the beverage becomes inaccurate.

(2) When a sealed container (for example, with large volume capacity) is shaken to agitate its content by means of a mechanical shaker, it is difficult to integrate with inspection equipment because the shaker is bulky and heavy.

(3) When the elastically deformable barrel portion of the sealed container is partially pressed in a horizontal direction to measure the pressing force and the displacement of the barrel portion, since the sealed container moves somewhat during the inspection, the frictional forces between its bottom portion and the container stand under the influence of its own weight adversely affect the measurement accuracy.

(4) Whether manually or by a large-size shaker, it takes a lot of time to agitate the content and higher measurement costs result.

Accordingly, a fourth aspect of the present invention is provided in view of the foregoing problems. Its object is to provide a small-size shaking apparatus used in the apparatus for non-destructively inspecting the content of the container, which allows the measuring accuracy of the internal pressure of the sealed container to be improved while further allowing the measuring time to be shortened.

In order to achieve the foregoing end, according to the fourth aspect of the present invention, there is provided a shaking apparatus used for non-destructively inspecting the content in a container, such as a can or sealed container made of a plastic material and having an elastically deformable barrel portion, the shaking apparatus shaking and agitating the content prior to the inspection of the internal pressure and the sugar content or the like of the container content including a water-soluble gas filled within, comprising a water tank for immersing a part of the container to be inspected into water, and a vibrator for transmitting the ultrasonic vibrations through the water within the water tank to the interior of the container from the lower portion of the water tank.

Further, the apparatus according to the fourth aspect of the present invention comprises a float for supporting the container to be inspected on the water surface of the water tank so that a part of the container can be immersed in the water in the water tank.

Based on the foregoing arrangement, the fourth aspect apparatus according to the present invention functions as follows.

That is, the container to be inspected (a can or a sealed container made of a plastic material having an elastically deformable barrel portion) filled with a foodstuff, beverage or the like is set in the water tank, and subsequently ultrasonic waves are generated from the vibrator provided at the bottom portion of the water tank. The ultrasonic waves are transmitted to the content of the container through the water in the water tank to shake and agitate the content for its uniformity. If the content is a carbonated beverage, then the content is brought into a gas-liquid equilibrium saturated state, and subsequently predetermined inspections and measurements can be carried out. At this time, if the container is retained through the float on the water level of the water tank, then the frictional force caused by the weight to the container does not work at all, and the alignment by a pinching tool of the inspection equipment becomes easy and more accurate measurements become possible.

According to the shaking apparatus used in the non-destructive inspection apparatus of the fourth aspect, since the content of the container (can or sealed container made of a plastic material having an elastically deformable barrel portion) is shaken and agitated over a predetermined period of time by ultrasonic waves of a predetermined frequency, as described above, the conditions for setting the gas and the liquid to an equilibrium state can be made constant, and the measuring accuracy of the pressure internal to the container can be improved.

In addition, since the content of the container to be measured is shaken and agitated by means of the ultrasonic vibrator, the shaking apparatus can be made small.

Still further, it is free of any mobile portion, and it can be easily integrated into an inspection apparatus. Thus, it becomes unnecessary to move the container for shaking and fixing the container for inspection, and time required for measurements can also be shortened.

In addition, since the float keeps the container floating in the water tank, frictional forces caused by the weight of the container are eliminated with the result that it becomes possible to readily carry out the centering by the container pinching tool to achieve an improvement in accuracy.

According to a fifth aspect of the present invention, the foregoing gas density measuring apparatus and/or sugar content measuring apparatus and the shaking apparatus are both provided in order to allow the gas density and/or sugar content to be measured after a sample is shaken.

In order to achieve this end, the apparatus according to the fifth aspect of the present invention has the following arrangement.

That is, in the gas density and/or sugar content measuring apparatus according to any one of the first the third aspect of the present invention, the gas density and/or sugar content apparatus comprises a water tank in which a part of the sealed container is immersed in water, and a vibrator for transmitting the ultrasonic wave to the interior of the foregoing sealed container through the water in the water tank from a lower portion of the water tank.

In addition, alternatively, the foregoing apparatus comprises a water tank in which a part of the sealed container in water, a float for supporting the sealed container at the water surface of the water tank to immerse a part of the sealed container in the water in the water tank, and a vibrator for transmitting the ultrasonic oscillation from under the water tank through the water in the water tank to the interior of the sealed container.

The invention will now be described in detail with reference to the accompanying drawings, wherein:

FIG. 4 is a graphical illustration of the relative rigidity, that is, the gradient characteristic when the variation factor relative to the displacement of the load (relative rigidity of the container) is shown taking the internal pressure as a constant;

FIG. 11 is a transverse top plan view of a pressing means 210 as viewed in the direction of arrow A of FIG. 10;

FIGS. 12A, 12B and 12C are practical cross-sectional views of a pressure-contact means 240 as viewed from the direction of arrow B of FIG. 10;

FIG. 13 is a schematic view illustrating a signal processing system in accordance with the invention;

FIG. 15 is a schematic cross-sectional view illustrating a first embodiment of the shaking apparatus used in conjunction with an apparatus for non-destructively inspecting the content of the container according to a fourth aspect of the present invention;

DETAILED DESCRIPTION OF THE PREFERRED EMBODIMENTS

Figure 1:
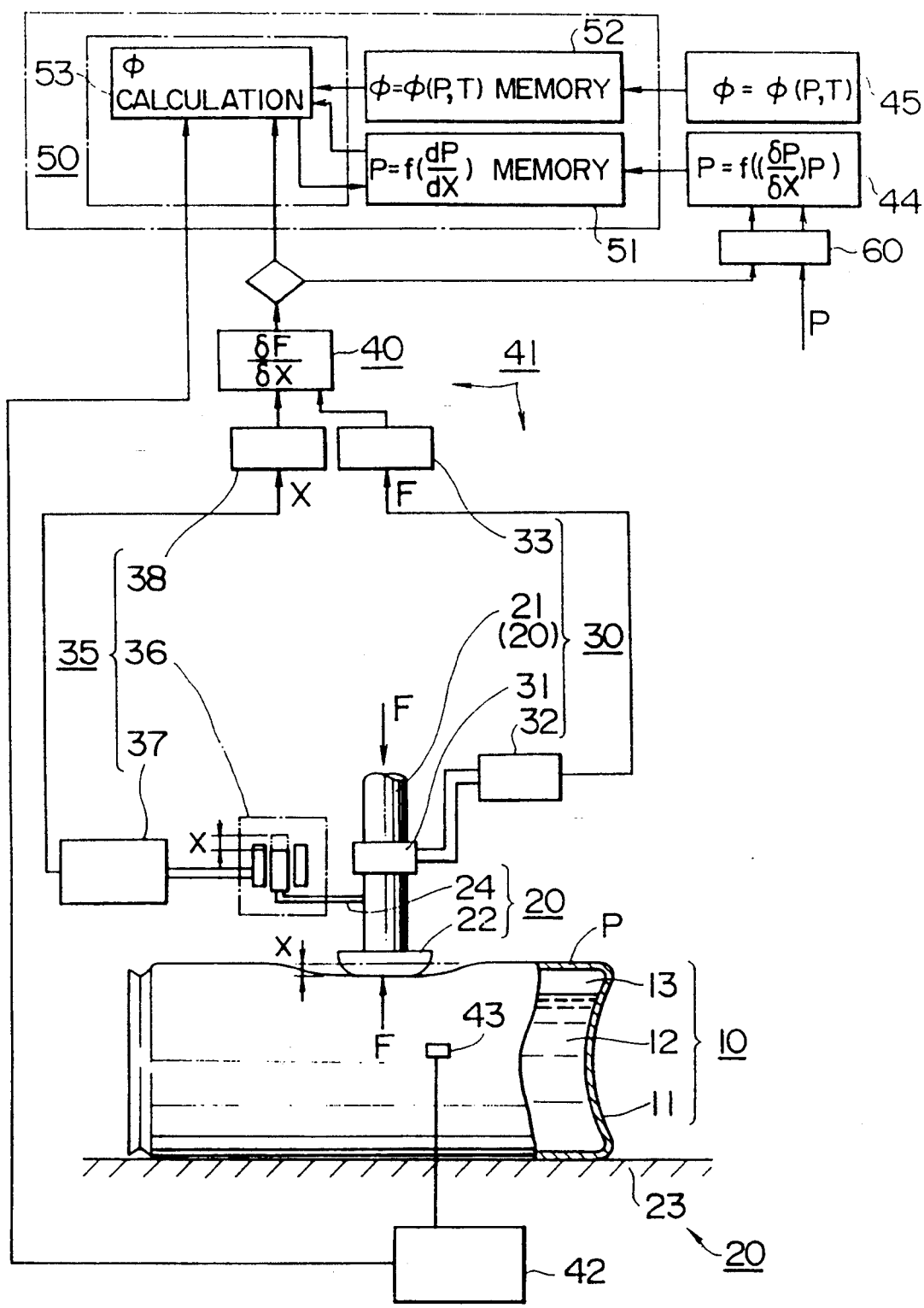
FIG. 1 is a schematic elevational view partly in cross section and an associated schematic circuit diagram illustrating an arrangement of pressure measuring apparatus used for practicing the method of measuring the pressure within the sealed container according to a first aspect of the present invention.

The arrangement according to the first aspect of the present invention is described with reference to FIG. 1. A container 10 of thin wall for sealing beverages comprises a container main body 11, a beverage (content) 12 filled within the container main body 11 and a gas phase portion 13 (gas phase portion of internal pressure P) within the container main body 11.

Further, reference numeral 20 denotes a pressing means for pressing a side lateral surface (or an end surface) of the foregoing container body 11, 21 a reciprocating ram of the pressing means 20, 22 a pressing member of the pressing means 21, 24 a support member mounted on the ram 22, and 23 a member for receiving and supporting the container against the force of the pressing means 20.

The pressing means 20 presses the container body 11 placed in the receiving member 23 by the reciprocating motion of the ram 21 and the pressing member 22.

In addition, reference numeral 30 denotes a load measuring means, 31 a load detecting member (for example, a load cell) of the load measuring means 30, and 32 a load signal processor of the load measuring means 30. The load detecting member 31 is interposed between the ram 21 of the foregoing pressing means 20 and the pressing member 22, and, when the ram and the pressing member 22 are reciprocatingly moved, the load measuring means 30 measures the load by utilizing the relationship between the load and the distortion imparted on a sample, which is obtained by the load detecting member 31, and the relationship between the distortion and variations of electrical characteristics. At that time, the load signal processor 32 receives the distortion corresponding to the load from the load detecting member (for example, the load cell) 31 as changes in the electrical characteristics to display the load value or output the electrical signal corresponding to that value.

Further, reference numeral 35 denotes a displacement measuring means, 36 a member for detecting the displacement of the displacement measuring means 35 (for example, an actuating transformer comprising a coil and a mobile core, or a pneumatic micrometer comprising a nozzle and a flapper), and the mobile core or flapper is supported by the support member 24 of the pressing means 20. A displacement signal processor 37 of the displacement measuring means 35 receives displacements of the mobile core or flapper as changes in inductance or in the back pressure of the nozzle, and displays the amount of displacement or sends out an electric signal corresponding to it.

A container rigidity calculation means 40 calculates the container rigidity $((\alpha F/\alpha X)_{p=p})$.

Reference numeral 41 denotes a means for non-destructively calculating the internal pressure p, which is comprised of pressing means 20, load measuring means 30, displacement means 35 and container rigidity calculation means 40.

Reference numeral 42 denotes a means for measuring the surface temperature of the sealed container 10, 43 a sensor, 44 a gradient characteristic and 45 a gas-liquid equilibrium density characteristic.

A gas-liquid equilibrium density calculation means 50 calculates the gas-liquid equilibrium density, and comprises a gradient characteristic storage means 51 for storing the gradient characteristic ($P=f(\alpha F/\alpha X)_p$), a gas-liquid equilibrium characteristic storage means 52 for storing the gas-liquid equilibrium characteristic ($\phi=\phi(P, T)$), and a density calculation means 53. Among these, the gradient characteristic storage means 51 stores the gradient characteristic 44 as a function. Further, the gas-liquid equilibrium characteristic storage means 52 stores the gas-liquid equilibrium density characteristic 45 as a function. When the internal pressure P of the container is unknown, the density calculation means 53 uses the output of the container rigidity calculation means 40 and that of the gradient characteristic storage means 51 to calculate the internal pressure P of the container. Using this calculated result (internal pressure P of the container) and the temperature T measured by the surface temperature measuring means 42, the gas-liquid equilibrium density $\phi$ is calculated.

Further, reference numeral 60 denotes an auxiliary calculation means, X a displacement (L), F a load (F), P an internal pressure ($F/M^2$), $G_p$ the relative rigidity of the container under the internal pressure of p, $G_{pj}$ the relative rigidity (F/L) of a J-th container under the internal pressure P, $\alpha/\alpha X$ a partial differential relative to X, T the temperature, and $\phi$ the gas-liquid equilibrium density.

Next, the function of the pressure measuring apparatus is concretely described. Within the sealed container 10, the beverage 12 is filled except for the gas phase portion 13, and the pressure (internal pressure) prevailing within the sealed container 10 is P. This sealed container 10 is placed on the receiving member 23 of the pressing means 20. Subsequently, changing the load F by the pressing means 20, the upper surface of the sealed container 10 is pressed to elastically deform the sealed container 10 to change the pressure (internal pressure) P therein.

On the other hand, the displacement X of the pressing means 20 is simultaneously measured by the displacement measuring means 35, the load F applied to the pressing means 20 is measured to obtain a relationship between the load F and the displacement X under various internal pressures while a variation factor characteristic relative to the displacement of the pressure (internal pressure) P and the load F is determined from this relationship to specify the pressure (internal pressure) P from this characteristic. This point is further concretely described with reference to FIGS. 2 and 3.

Figure 2:
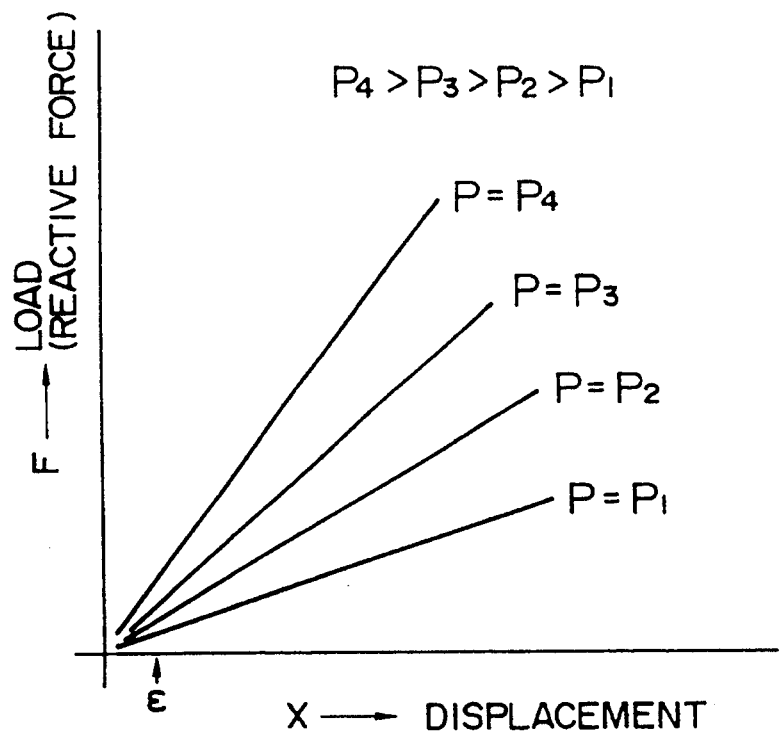
FIG. 2 is a graphical illustration of the relationship between the load and the displacement with the internal pressure taken as a parameter, that is, a weight-displacement characteristic.

FIG. 2 illustrates an example of the result obtained by measuring the relationship between the load F and the displacement X by changing the pressure (internal pressure) P of the sealed container 10. From this, it can be found that, if the pressure (internal pressure) P lies within a specific range relative to a specific sealed container 10, $(\alpha F/\alpha X)_p$ becomes constant.

Figure 3:
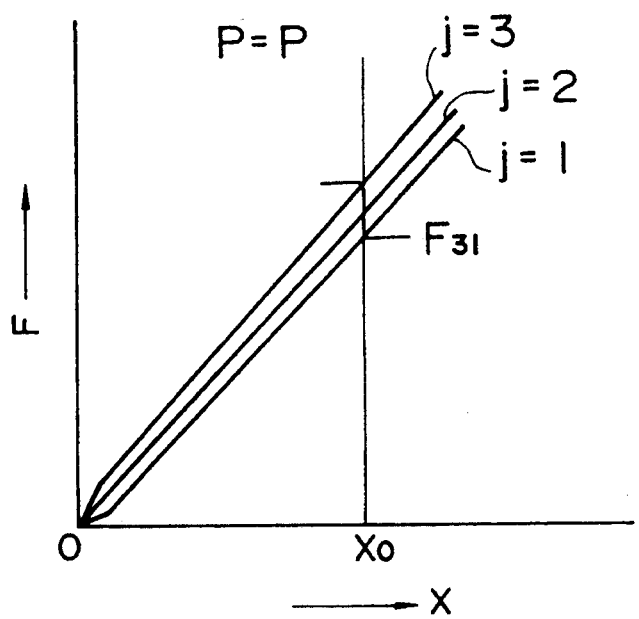
FIG. 3 is a graphical illustration of the load-displacement characteristic relative to a specific internal pressure.

FIG. 3 is an illustration of the F-X characteristic relative to the same sealed container 10 with J=3 including an enlargement in the neighborhood of X=0. From this, it is found that:

(1) $(\alpha F/\alpha X)_{p,j=1} \approx (\alpha F/\alpha X)_{p,j=2} \approx (\alpha F/\alpha X)_{p,j=3}$
where $X > \epsilon > O$, $\epsilon$ is an appropriate value; and (2) If $X \approx O$, $(\alpha F/\alpha X)_p$ is indefinite. Therefore, with this state held, the inferred error of P is large.

FIG. 4 illustrates the gradient characteristic of a specific sealed container 10. From this, it is found that, if a sealed container 10 is specified, the gradient characteristic can be uniquely determined from the following relationship:

(3) $P=f((\alpha F/\alpha X)_p)$.

Thus, if the foregoing relationship (3) is previously evaluated according to the kind of the sealed container 10, the pressure (internal pressure) P within the sealed container 10 can be non-destructively evaluated.

This is the function of the non-destructive internal pressure calculation means 41 when the internal pressure P of the container is treated as known.

In addition, if the internal pressure P of the container is treated as known, the output of the container rigidity calculation means 40 is entered into the gas-liquid equilibrium density calculation means 50.

At this time, the gradient characteristic storage means 51 of the gas-liquid density calculation means 50 stores the gradient characteristic 44 as a function. In addition, the gas-liquid equilibrium characteristic storage means 52 stores the gas-liquid density characteristic 45 as a function. Further, when the internal pressure P of the container is unknown, the density calculation means 53 uses the output of the container rigidity calculation means 40 and that of the gradient characteristic storage means 51 to calculate the internal pressure P of the container, and, using this calculated result (internal pressure P) and the temperature T measured by the surface temperature measuring means 42, it calculates the gas-liquid equilibrium density (that is, the gas density within the beverage within the sealed container 10 is measured).

Next, the sugar content measuring apparatus according to the second aspect of the present invention is described with reference to the embodiments of FIGS. 6 through 8. Reference numeral 100 in FIGS. 6 and 7 denotes a sealed container of thin wall which is made of a metal or a plastic, 101 a beverage existing within the sealed container 100, 110 and 120 sensor holders opposing to each other with the sealed container to be measured positioned therebetween, 130 an air cylinder (press-contact means) for shifting the sensor holder 120 in the direction of arrow, 131 a solenoid valve for switching the air pressure circuit of the air cylinder 130, 132 a supply source of pressurized air, and 140 a measuring stand for supporting the sealed container 100.

To the foregoing sensor holder 110, a wave sender 111 of the ultrasonic wave sensor (or a wave sender/receiver 111' working both as a wave sender and receiver) and the container surface temperature sensor 121 are mounted. On the foregoing sensor holder 120, a wave receiver 112 of the ultrasonic wave sensor is mounted. In addition, in the neighborhood of the sealed container set at the measuring position, an ambient temperature sensor 122 is disposed.

Reference numeral 150 denotes an ultrasonic wave timing means, which is connected to the wave sender 111 and the wave receiver 112. Reference numeral 160 denotes a calculation control means, 170 a monitor (display means), 171 a printer (display means) and 172 a keyboard. The calculation control means 160 is connected to the ultrasonic timing means 150, the container surface temperature sensor 121, the ambient temperature sensor 122, and the solenoid valve 131.

Figure 8:
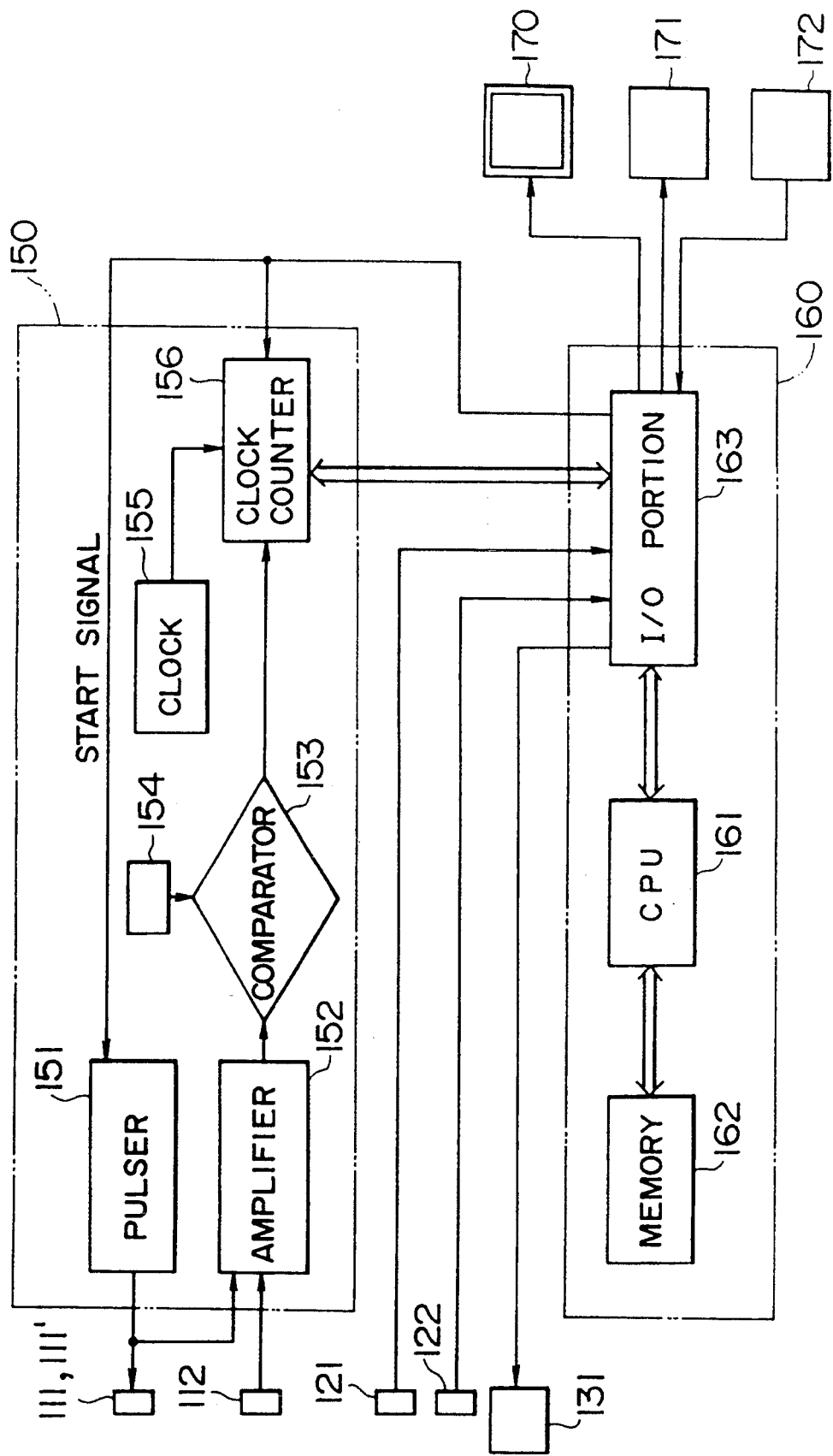
FIG. 8 is a diagram illustrating an ultrasonic wave timing means and a calculation control means in detail.

FIG. 8 illustrates the detail of the ultrasonic timing means 150 and the calculation control means 160. First, referring to the elements at the side of the ultrasonic timing means 150, 151 denotes a pulser, 152 an amplifier, 153 a comparator, 154 a reference voltage setter, 155 a clock for generating clock pulse, and 156 a clock counter. Next, referring to the calculation control means 160, reference numeral 161 denotes a CPU, 162 a memory, and 163 an input/output (I/O) portion.

Figure 6:
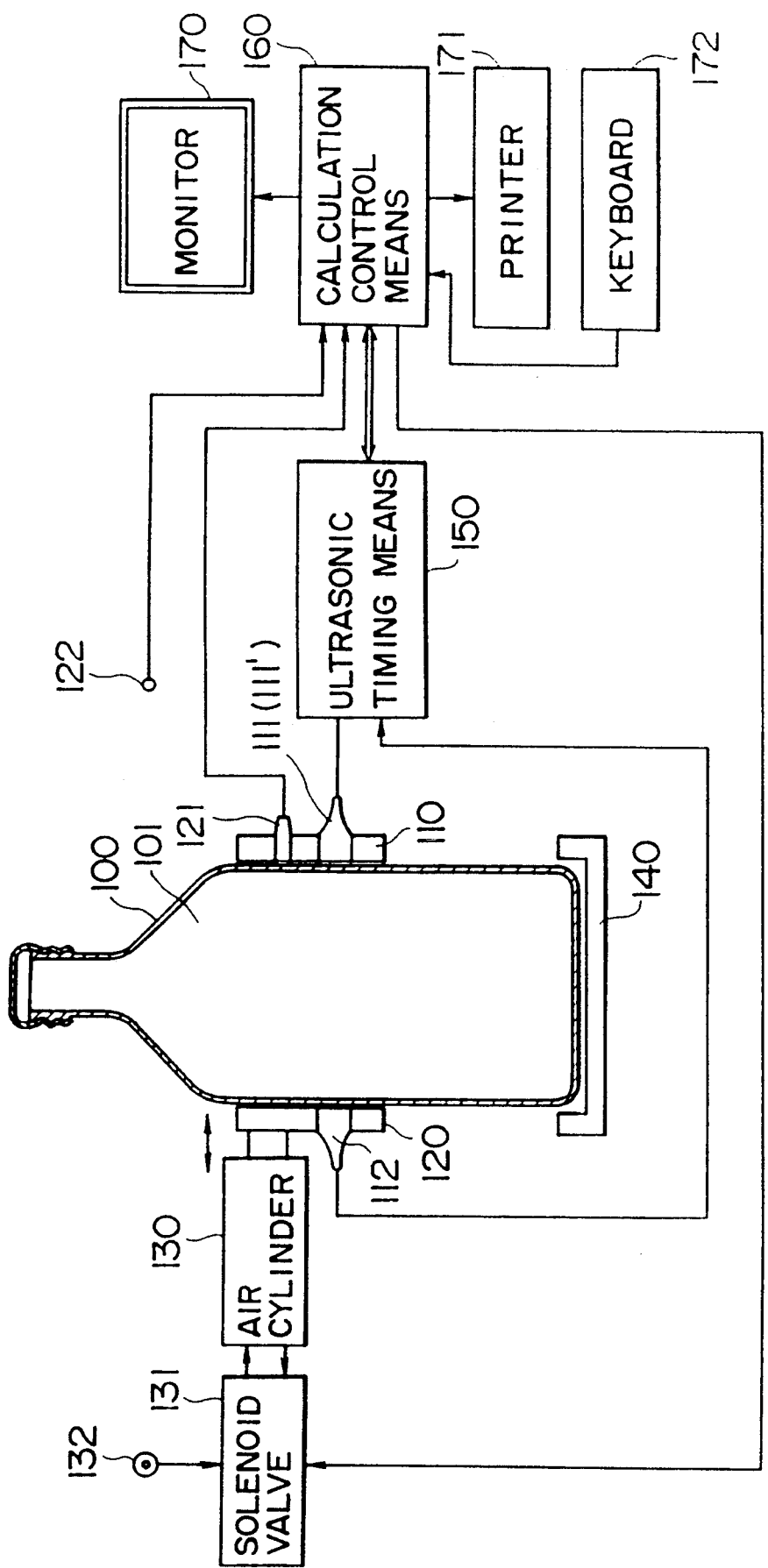
FIG. 6 is a schematic view and associated circuit diagram illustrating a specific example of the sugar content measuring apparatus according to a second aspect of the present invention.
Figure 7:
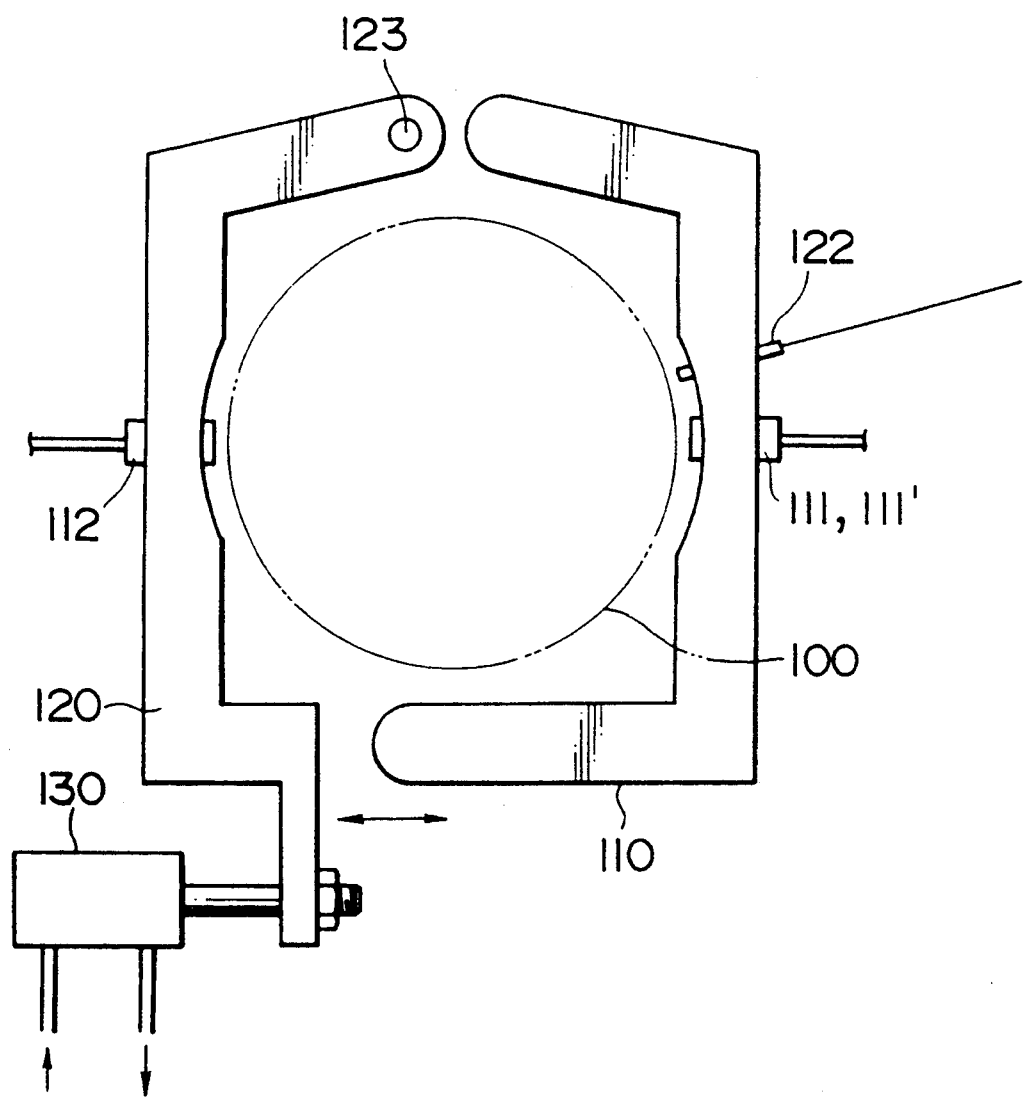
FIG. 7 is a schematic plan view partially illustrating an ultrasonic sensor, temperature sensor and pressure-contact means.

Next, the operation of the sugar content measuring apparatus shown in FIGS. 6 through 8 is specifically described.

First, the sealed container 100 to be measured is placed on the measuring stand 140, and a start timing is entered from the keyboard 172 to the input/output portion 163 of the calculation control means 160. A signal is sent out from the input/output portion 163 to the solenoid valve 131.

This signal causes the solenoid valve 131 to be switched to actuate the air cylinder 130 in the extending direction to rock the sensor holder 120 toward the container with the rocking center point 123 as its axis so that the sensor holder 120 and the wave receiver 112 of the ultrasonic sensor may press-contact the surface of the sealed container 100. At this time, the wave sender 111 of the ultrasonic sensor and the container surface temperature sensor 121 also press-contact the surface of the sealed container 100.

Next, a measuring start signal pulse is outputted from the input/output portion 163 of the calculation control means 160 to the clock counter 156 and the pulser 151 of the ultrasonic timing means 150. Upon receipt of the pulse, the clock counter 156 starts to count the clock pulse from the clock 155. On the other hand, the pulser 151, upon receipt of the measuring start signal pulse, converts this into a high voltage pulse, and sends it to the wave sender 111 (or to the wave sender/receiver 111' serving as both a wave sender and a wave receiver).

Upon receipt of the high voltage pulse, the wave sender 111 of the ultrasonic sensor converts this into a pressure wave of a frequency in the ultrasonic range to radiate it into the beverage within the sealed container. This pressure wave propagates through the beverage 101 within the sealed container 100 to enter the wave receiver 112 of the ultrasonic sensor. Incidentally, when the wave sender/receiver 111' is provided, it is reflected against the wall surface of the container and returned to the wave sender/receiver 111'.

Figure 9:
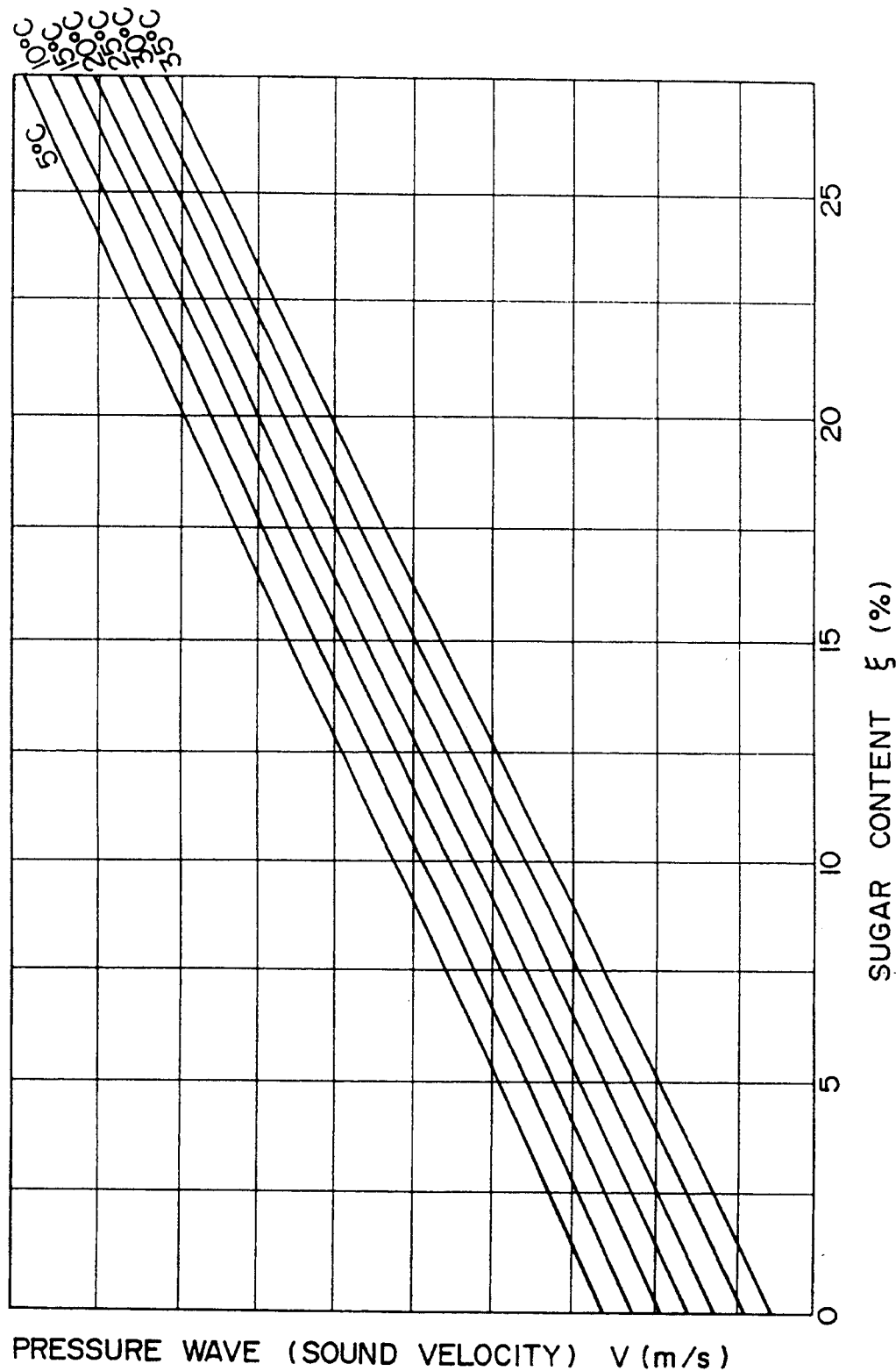
FIG. 9 is graphical illustration of the relationship between the pressure wave and the sugar content.

The propagation velocity V of the pressure wave which is radiated into the beverage 101 is uniquely determined by the sugar content $\xi$ and the temperature t of the beverage 101, as shown in FIG. 9. On the other hand, since the distance L between the wave sender 111 and the wave receiver 112 of the ultrasonic sensor (or the distance L' between the wave sender/receiver 111' and the opposing wall surface of the container L'=2L) is made constant by the press-contact of the air cylinder 130, the propagation time becomes as follows according to the sugar content $\xi$ and the temperature t of the beverage 101.

$\tau = L/V$ (when the pressure wave propagates from the wave sender 111 to the wave receiver 112).

$\tau' = 2 \cdot L/V$ (when the pressure wave propagates from the wave sender/receiver 111' through the wall surface the container to the wave sender/receiver 111').

When the foregoing pressure wave enters the wave receiver 112 (or the wave sender/receiver 111'), the pressure wave is converted into an electric signal. This signal outputted to an amplifier 152 of the ultrasonic timing means 150 in which it is amplified with a certain magnifying factor and is outputted to the comparator 153 as a voltage signal. In this comparator, the signal voltage and the preset voltage from the comparative voltage setter 154 are compared with each other, and, if the former is higher than the latter (it becomes higher than the comparative voltage when the ultrasonic wave is received), a signal of certain level is outputted to the clock counter 156.

When the foregoing signal of certain level comes in, this clock counter 156 stops counting the clock, and ends the timing of the propagation time $\tau$ or $\tau'$ with its clock count value N being held. Incidentally, $\tau$ or $\tau'$ is determined according to a relationship of $\tau = N/f$ (or, $\tau' = N/f$), and f is determined according to the clock frequency.

The calculation control means 160, after a predetermined period of time since the foregoing timing start signal pulse is sent, outputs a reset signal from an input/output portion 163 to a clock counter 156, when the clock count value (timed value) enters the input/output portion 163 from the input/output portion 163. At this point of time, the clock counter 156, receiving the reset signal, resets the timed value.

The foregoing calculation control means 160 converts the signal (voltage) corresponding to the temperature, which is sent from the container surface temperature sensor 121 and the ambient temperature sensor 122, from the analog into the digital form to calibrate the value $t_w$ of the container surface temperature and the ambient temperature value $t_a$. Further, a signal is sent from the input/output portion 163 of the calculation control means 160 to the solenoid valve 131 to switch the latter to actuate the air cylinder 130 in the retracting direction so that the sensor holder 120 swings in a direction opposite to the container with the swinging center point 123. The sensor holder 120 and the wave receiver 112 of the ultrasonic sensor are separated from the surface of the sealed container 100 to release the sealed container 100.

The foregoing calculation control means 160 calculates the temperature t of the beverage 101 within the sealed container 100 based on the value $t_w$ of the container surface temperature and the ambient temperature value $t_a$, which correspond to the foregoing input data.

In addition, based on the foregoing timed value N and the predetermined propagating distance L (or L'), the propagation velocity V of the pressure wave is calculated (for example, $V = L/\tau$, $\tau = N/f$). Further, based on the calculated beverage temperature t and propagation velocity V, the sugar content $\xi$ of the beverage 101 is calculated to display on a monitor 170, which is a means for displaying sugar content, while recording by means of a printer 172.

Incidentally, these execution programs and the data necessary for calculation (for example, $V = v(t, \xi)$, $t = t(t_a, t_w)$ and the like) are stored in the memory 162 beforehand.

Figure 10:
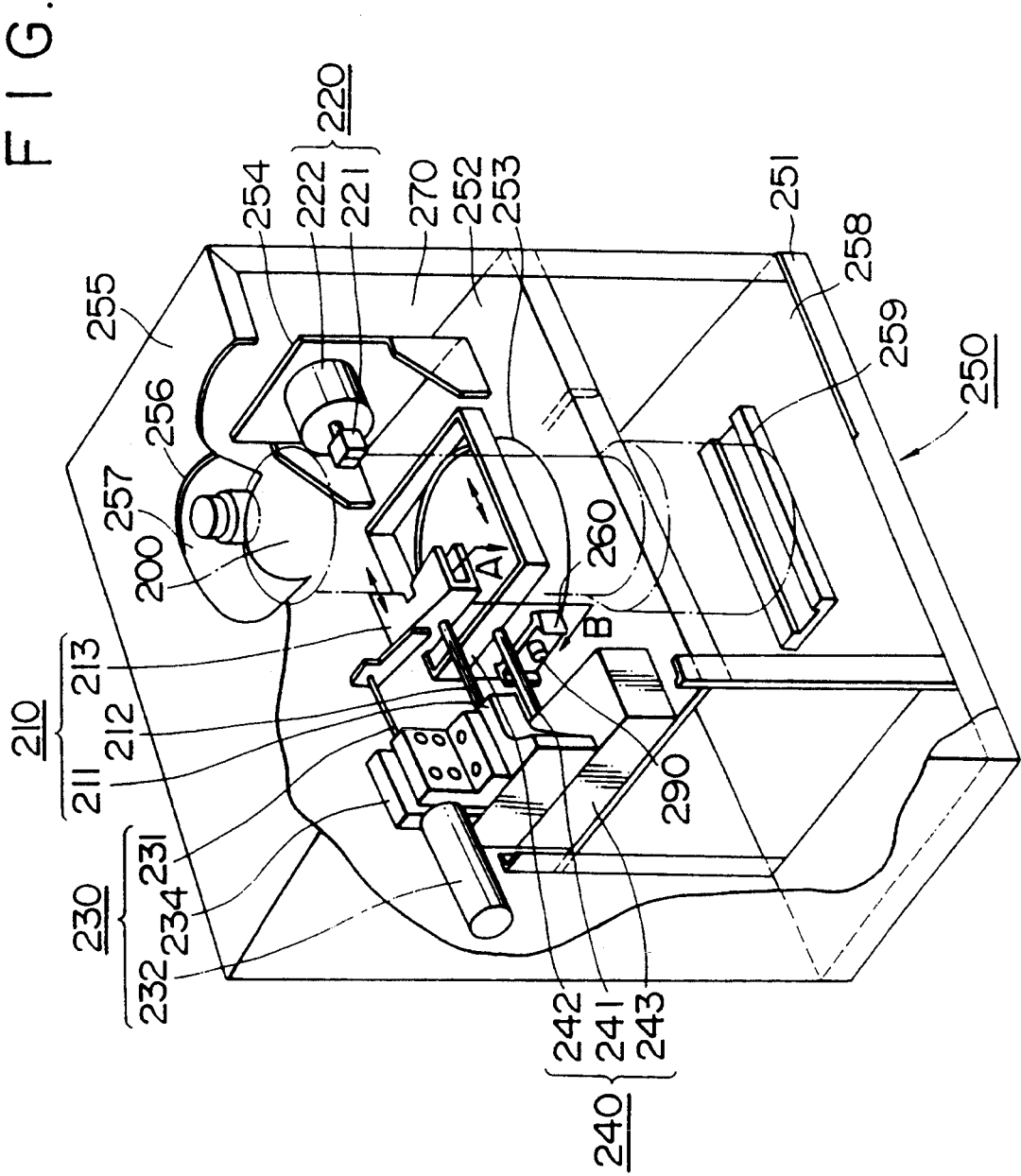
FIG. 10 is a schematic perspective view illustrating a specific example of an apparatus for simultaneously measuring the sugar content and the gas density according to a third aspect of the present invention.

Next, the apparatus for simultaneously measuring the sugar content and gas density of a beverage according to the third aspect of the invention is explained according to two specific embodiments illustrated in FIGS. 10 through 13. FIG. 10 is a perspective view illustrating the measuring apparatus. FIG. 11 is a crosswise plan view of the pressing means 210 as viewed in the direction of arrow A of FIG. 10. FIGS. 12A and 12B are longitudinal lateral views of the press-contact means 240, as viewed in the direction of arrow B of FIG. 10 in the two embodiments of the third aspect of the present invention. FIG. 12C is to show details of the cross-section of the second embodiment in correspondence with FIG. 12B. FIG. 13 is a circuit diagram of a signal processing system.

In FIGS. 10 through 13, reference numeral 200 denotes a sealed container, 201 a container main body, 202 a beverage liquid within the sealed container 200 (such as carbonated beverage or the like), and 203 a gas in the gaseous phase within the sealed container 200.

The pressing means 210 has cylinder 211, a piston 212, and a block 213 of U-shaped cross section.

A load measuring means 220 has a load cell 221, a converter 222, and an A/D converter 223 (see FIG. 13).

Reference numeral 230 denotes a displacement measuring means for measuring the displacement of the pressing means 210, and it has a stylus (follower rod) 231, a converter 232, an A/D converter 223 (see FIG. 13) and a support member 234.

The pressing means 240 has a piston 241, a frame 242 attached to the piston 241 and cylinder 243. Also, in FIGS. 12B and 12C, another ultrasonic vibrator 291 is mounted on the pressing means 240.

A box-shaped container stand 250 has a frame 251, a partitioning member 252, a container inlet hole 253 provided through the partitioning member 252, a bracket 254 for mounting the load measuring means 220 (described later), a container inlet hole 256 having a conical cover member 255, a container guide member 257 mounted about the inlet hole 256, a bottom member, a container member 259 mounted on the bottom member 258, and a container positioner member 260 mounted on the partitioning member 252.

A detector 270 of the ambient temperature detects the ambient temperature $t_a$ of the sealed container 200. The surface temperature detecting means 280 (FIG. 11) detects the surface temperature $t_w$ of the sealed container 200. An ultrasonic vibrator 290 for sending waves, which also serves as a wave receiver, is vibrated by an ultrasonic shaker 425 to induce elastic waves in the ultrasonic range to the sealed container 200. Incidentally, although the ultrasonic vibrator 290 serves as a wave sender and receiver, an ultrasonic vibration for sending waves and an ultrasonic vibration for receiving waves may be separately provided.

Reference numeral 400 (see FIG. 13) denotes a control means, 410 a density calculation control means, and 414 a container rigidity calculation means, calculates the container rigidity $k_p=(\alpha F/\alpha X)_p$ according to the pressing force F of the pressing means 210 and the displacement X of the displacement measuring means 230.

A gas-liquid phase equilibrium characteristic storage means 412 stores the gaseous phase equilibrium density characteristic $\phi=\phi(P, t)$ determined according to the kind of the beverage liquid 202, the internal pressure P of the container and the temperature t of the liquid within the container. Further, the container rigidity characteristic storage means 413 stores a relationship $P=P(k_p)$ between the internal pressure P of the container and the container rigidity $k_p$. Still further, the temperature characteristic storage means 416 stores the relationship $t=t(t_w, t_a)$ among the container surface temperature $t_w$, container ambient temperature $t_a$ and the liquid temperature t within the container.

The temperature characteristic calculation means 415 calculates the liquid temperature t in the container according to the relationship $t=t(t_w, t_a)$ among the container surface temperature $t_w$, the container ambient temperature $t_a$, and the liquid temperature t inside the container.

The gas-liquid equilibrium density calculation means 411, after calculating the internal pressure P in the container from the container rigidity $k_p$ outputted from the container rigidity calculation means 414, calculates the gas density $\phi$ in an equilibrium state between the liquid and the gas based on this internal pressure P of the container, the liquid temperature t inside the container which is outputted from the temperature characteristic calculation means 415 and $\phi=\phi(P, t)$ and outputs the results of the calculation.

Reference numeral 420 denotes a sugar content calculation control means, 421 an arithmetic processing portion, 422 an ultrasonic characteristic storage means for storing a relationship $V=v(t, \xi)$ among the propagation velocity V of the ultrasonic wave, the liquid temperature t within the container and the sugar content $\xi$, 423 an I/O interface, 425 an ultrasonic shaker means, 426 a clock circuit, 427 a clock pulse counter, 428 an amplifying detector circuit for amplifying the electrical output from the ultrasonic vibrator 290 and detecting an envelope thereof, 429 a circuit for calculating the propagation time, 430 a means for calculating the propagation velocity V of the ultrasonic wave in the beverage 202 from the outputs from the shaker 425 and the ultrasonic detector 428, and 431 a sugar content calculation means for calculating the sugar content of the beverage 202 from the propagation velocity V of the ultrasonic wave, the liquid temperature t within the container and the foregoing relationship $V=v(t, \xi)$.

Figure 14:
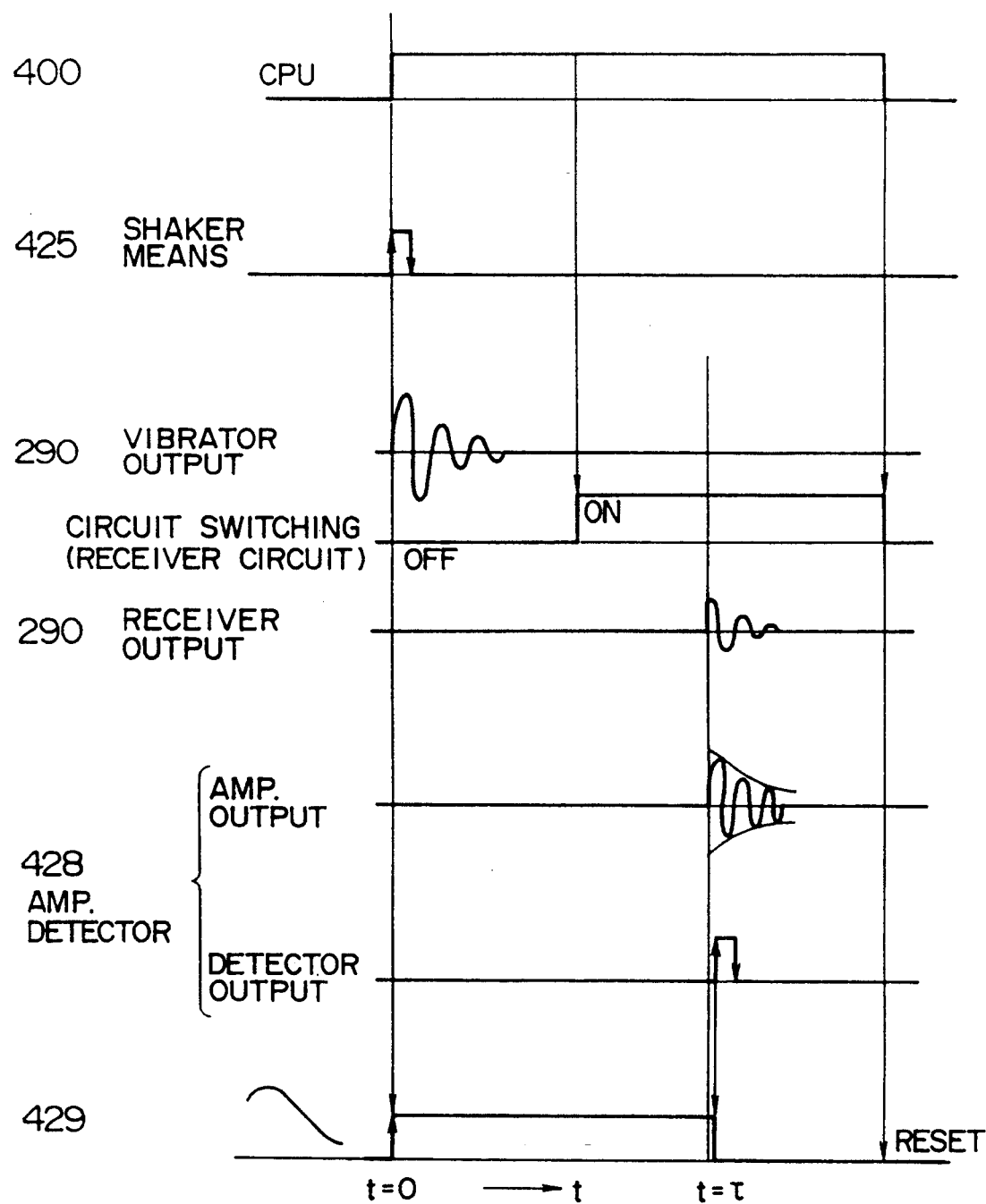
FIG. 14 is graphical illustration of the relationship between the wave movement and the propagation time.

FIG. 14 is an explanatory diagrammatic view illustrating the relationship between the wave motion and the propagation time.

Next, the operation of the apparatus shown in FIGS. 10 through 13 is specifically described.

(1) Calculation of the liquid temperature t of the sealed container 200:

The relationship among the surface temperature $t_w$ of the sealed container, the ambient temperature and the liquid temperature t inside the sealed container 200 can be determined by measuring beforehand. The relationship used when the liquid temperature t of the sealed container 200 is calculated as follows.

$$t=t(t_w, t_a) \quad \text{Eq. 1}$$

A contact type surface thermometer is used for the surface temperature detecting means, and a conventional resistance type thermometer is used for the ambient temperature detecting means of the sealed container 200 to detect the surface temperature $t_w$ of the sealed container 200 and the ambient temperature $t_a$ to calculate the liquid temperature t of the sealed container 200 according to the foregoing relationship.

(2) Calculation of the internal pressure P of the sealed container 200:

Changing the force applied to the lateral wall of the container body 201 with the internal pressure P of the sealed container 200 constant, the lateral wall of the container body 201 is pressed by means of the pressing means 210 to examine a relationship between the pressing force F and the resultant displacement X of the pressing means 210. At this time, when the displacement of the container body 201 (X) is not so great, it can be found that $\alpha F/\alpha X$ is approximately constant. The rigidity characteristic $k_p$ of this sealed container 200 is represented as follows.

$$k_p = (\alpha F/\alpha X)_p \qquad \text{Eq. 2}$$

However, since circumstances at the moment when the pressing means 210 starts to come in contact with the sealed container 200 are complicated, the relationship between the pressing force F and the displacement X is difficult to uniquely determine. On the other hand, if, taking the internal pressure P of the container as a parameter, $k_p$ is evaluated beforehand, then the internal pressure P of the container can be uniquely determined according to:

$$P = f(k_p) \qquad \text{Eq. 3}$$

This is shown in FIG. 4.

The pressing means 210 forces the sealed container 200 against the load measuring means 220 with varying pressing forces F. A linear scale interlocking with the pressing means 210 is used, for example, for the displacement measuring means 230, and the load cell 221 is used, for example, for the load measuring means 220. If the resultant detected value is entered via the A/D converters 223 and 233 to the container rigidity calculation means 414 then it calculates the container rigidity $k_p = (\alpha F/\alpha X)_p = \alpha F/\alpha X$ according to the pressing force F of the pressing means 210 and the displacement X of the displacement measuring means 230 to evaluate the container rigidity $k_p$.

Figure 5:
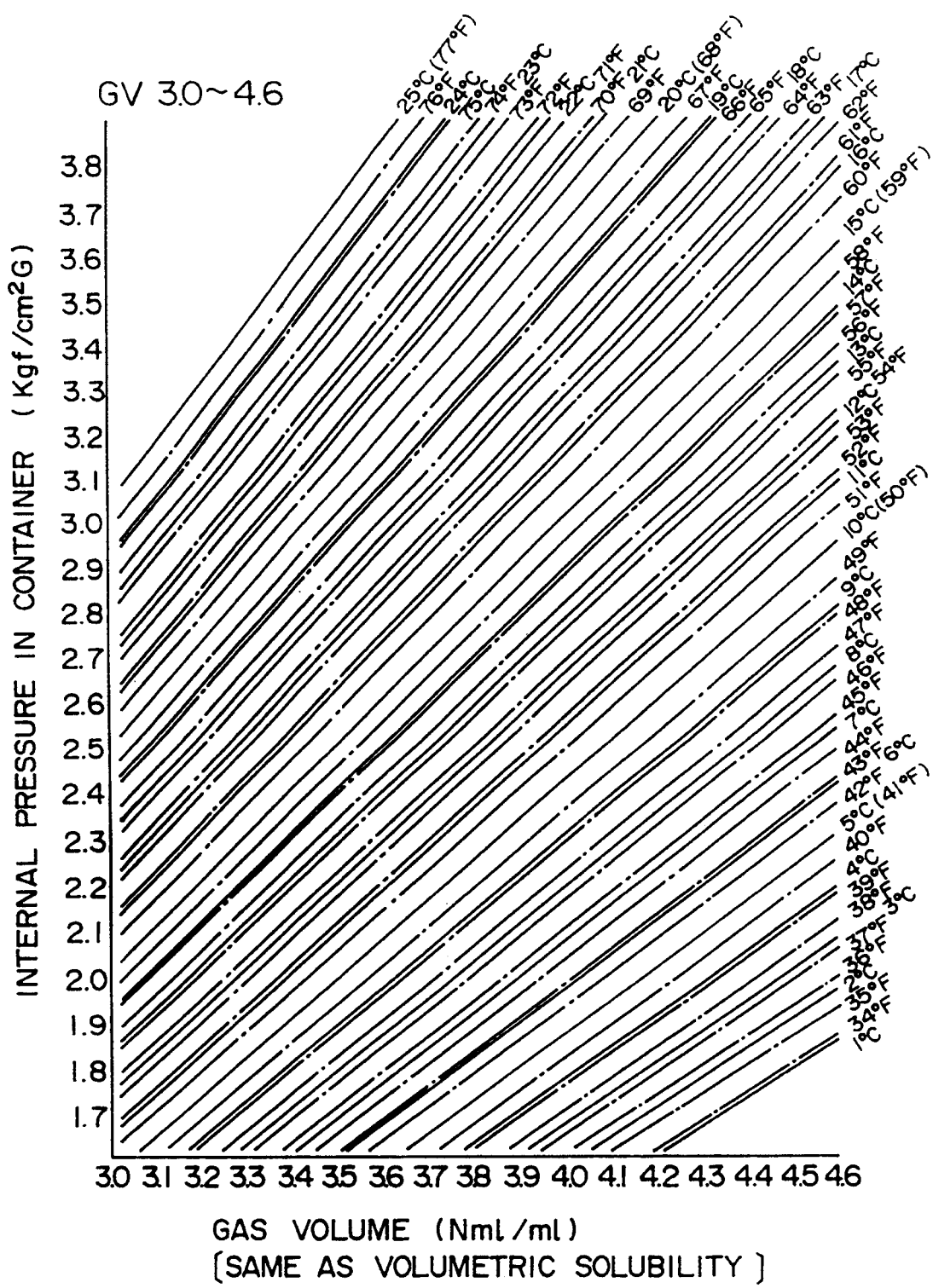
FIG. 5 is a graphical illustration of a specific example of the gas-liquid equilibrium density characteristic.

(3) Calculation of the gas density $\phi$:

When the beverage liquid 202 and the gas 203 within the sealed container 200 lie in an equilibrium state, the density of the gas 203 within the beverage 202, if the container pressure P and the liquid temperature t are known, is uniquely determined. This is shown in FIG. 5. The density $\phi$ of the gas 203 in the beverage 202 is represented as follows:

$$\phi = \phi(P, t) \qquad \text{Eq. 4}$$

When the beverage liquid 202 and the gas 203 in the sealed container 200 lie in an equilibrium state, the internal pressure P of the container and the liquid temperature t are calculated according to the foregoing Eq. 3, and the gas density is then calculated according to the foregoing Eq. 4.

The temperature characteristic storage means 416 stores the liquid temperature t according to foregoing Eq. 1 ($t = t(t_w, t_a)$). The container rigidity characteristic storage means 413 stores the rigidity characteristic according to foregoing Eq. 3 ($P = f(k_p)$), and the density characteristic storage means 412 stores the Eq. 4 ($\phi = \phi(P, t)$).

The temperature characteristic calculation means 415, calculates the liquid temperature t within the container according to the relationship $t = t(t_w, t_a)$ among the container surface temperature $t_w$, the container ambient temperature $t_a$ and the liquid temperature t in the container. The gas-liquid equilibrium density calculation means 411, after the internal pressure P within the container is calculated from the container rigidity $k_p$ obtained by the container rigidity calculation means 414, calculates the gas density $\phi$ at which the liquid and the gas lie in an equilibrium state from the container internal pressure P, liquid temperature t in the container outputted by the temperature characteristic calculation means 415 and from the gas-liquid density characteristic $\phi = \phi(P, t)$.

(4) Calculation of the sound velocity characteristic:

The sound velocity V within the beverage liquid 202 equals the propagation velocity of the elastic wave movement, and is represented by:

$$V = \sqrt{\{E/\rho\}} \qquad \text{Eq. 5}$$

where E is the modulus of elasticity of the liquid, and $\rho$ is the density of the liquid.

For the liquid into which the air is dissolved, strictly speaking, both E and $\rho$ change. However, for a normal range of beverage liquids, the sound velocity V in the liquids is negligibly affected by the solubility of the gas, and strongly affected by the temperature.

Further, since, in general, the solubility of the solvent greatly varies with the temperature, the dissolving characteristic, that is, the relationship between the sugar content and the sound velocity V, or the sound velocity characteristic can be evaluated beforehand according to an experimental or theoretical method. This sound velocity characteristic is assumed as follows.

$$V = v(t, \xi) \qquad \text{Eq. 6}$$

This is shown in FIG. 9.

Since the liquid temperature t within the container is obtained from Eq. 1, if V is measured, then sugar content $\xi$ is evaluated.

(5) Calculation of the sound velocity V:

If an electric field is applied to a piezoelectric material, a mechanical distortion occurs in a specific direction relative to the electric field. Further, if the load is applied to one surface of the piezoelectric material and a mechanical distortion is given, then a voltage output results. Utilizing this principle, if a single pulse voltage is applied to the piezoelectric material as a vibrator on the lateral wall of the sealed container 200, then a pulsed distortion takes place on the lateral wall of the sealed container 200 which propagates through the beverage liquid 202 within the sealed container 200 as an elastic wave and enters the opposed lateral wall of the sealed container 200. A part of the elastic wave is transmitted through the lateral wall and the remainder is reflected back. Since these transmitted wave and reflective wave are pressure waves, it imparts a distortion to the piezoelectric material provided at a predetermined position, and a voltage output results therefrom. If the voltage output of the piezoelectric material is amplified and sliced with a proper threshold value, then a pulse of the pressure wave results.

If the foregoing piezoelectric material is used for sending and receiving waves, then the generation of the pressure wave and the detection of the propagating pressure wave can be carried out.

If the gate of the clock circuit 426 is opened by the pulse voltage signal and the gate is closed by the detected pulse of the pressure wave, then the time $\tau$ required for the pressure wave to propagate is measured.

In addition, since the size of the sealed container 200 is known, assuming that the diameter of the sealed container 200 is D, and the propagation distance of the pressure wave is L, it is determined with these factors which of either the penetrating wave or the reflected wave should be adopted:

$$L = D \text{ or } 2 \cdot D \qquad \text{Eq. 7}$$

The propagation time $\tau$ of the distance L is evaluated according to the foregoing teaching. The sound velocity V is evaluated according to the following formula.

$$V = L/\tau \qquad \text{Eq. 8}$$

Since the liquid temperature t within the container and the sound velocity V can be evaluated from Eq. 1 and Eq. 8 respectively, the foregoing Eq. 6 is inversely calculated to evaluate the sugar content $\xi$.

$$x = v^{-1}(t, \xi) \qquad \text{Eq. 9}$$

In addition, in the case of using the wave penetrating through the container 200, the sugar content $\xi$ can be calculated with further accuracy in the following manner.

Figure 12B:
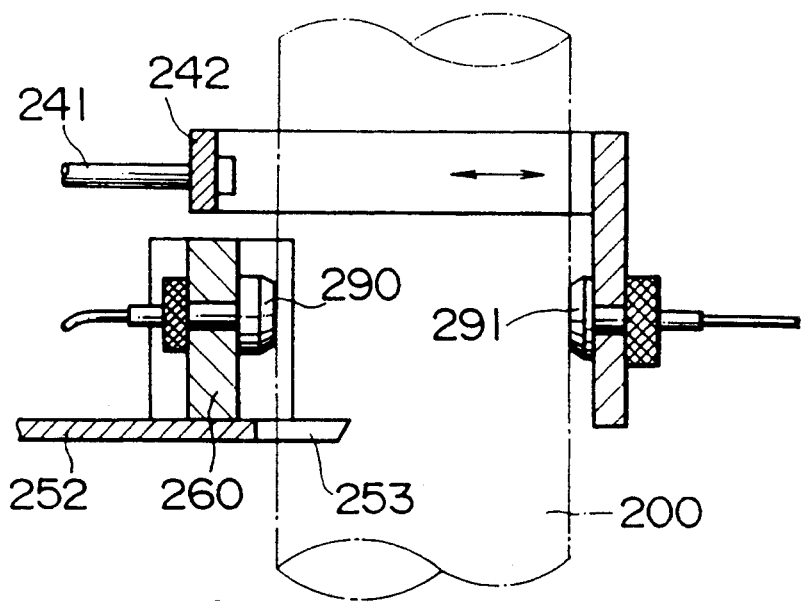
Figure 12C:
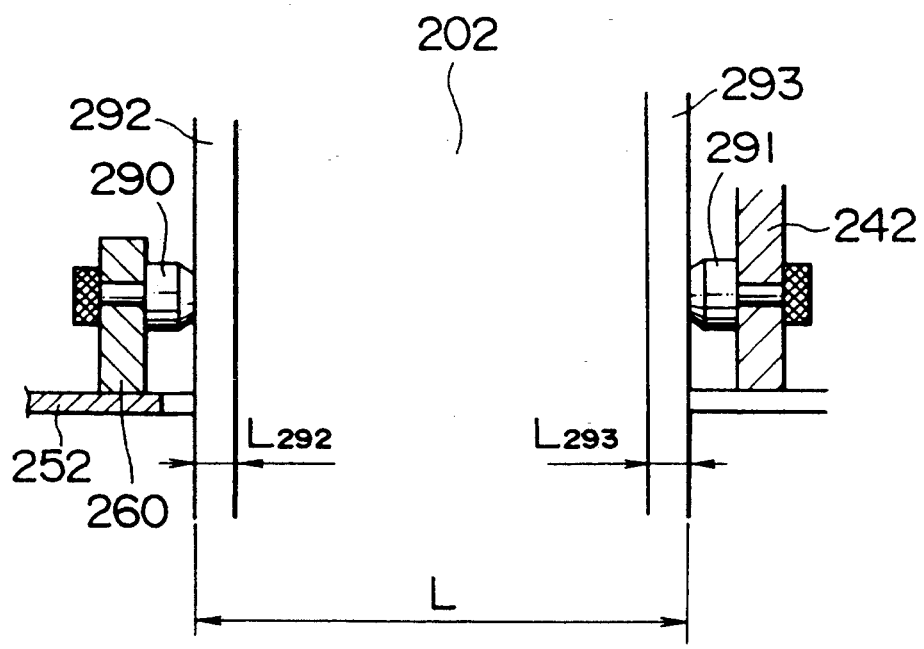

The ultrasonic vibrator (as a sender sensor) 290 and the ultrasonic vibrator (as a receiver sensor) 291 are set oppositely as shown in FIGS. 12A, 12B, and 13. The ultrasonic pulse transmitted by the vibrator (as a sender sensor) 290 penetrates the lateral wall 292 of the sealed container 200, the beverage liquid 202 and the lateral wall 293 of the sealed container 200, and it is received by the ultrasonic vibrator (as a receiver sensor) 291. Assuming that the propagation delay time of the lateral wall 292, lateral wall 293 and beverage liquid 202 be $t_{292}$, $t_{293}$ and $t_{202}$ respectively, the propagation delay time between the ultrasonic vibrators 290 and 291 is equal to $t_{292} + t_{202} + t_{293}$.

Assuming that the distance between the ultrasonic vibrators 290 and 291 is L, the thickness of the lateral wall 292 and 293 are $L_{292}$ and $L_{293}$, respectively, and the propagation distance of the beverage liquid be $L_{202}$, L is equal to $L_{292} + L_{202} + L_{293}$.

The propagation delay time $t(\tau)$ is equal to $t_{292} + t_{202} + t_{293}$.

The sound velocity V can be evaluated according to the following formula:

$$V = \frac{L - (L_{292} + L_{202})}{L - (t_{292} + t_{293})} \qquad \text{Eq. 10}$$

The time $t_{292}$ is equal to a half of the time required for the pulse transmitted by the ultrasonic vibrator (as a sender sensor) 290 to return after reflecting at the boundary between the lateral wall 292 and the beverage liquid 202. The time $t_{293}$ is a half of the time required when the pulse transmitted by the ultrasonic vibrator (as a receiver sensor) 291, which is used as a sender sensor, returns back after reflecting at the boundary between the lateral wall 293 and the beverage liquid 202.

Since the material of the lateral wall is known, the sound velocity $V_p$ in the wall can be evaluated beforehand. Therefore, the thickness $L_{292}$ and $L_{293}$ of the lateral walls 292 and 293 of the sealed container 200 are evaluated according to the following formula.

$$L_{292} = t_{292} \times V_p \qquad \text{Eq. 11}$$

$$L_{293} = t_{293} \times V_p \qquad \text{Eq. 11}$$

As shown in FIG. 13, if the reflected wave is used, the pulse transmitted by the ultrasonic vibrator (as a sender sensor) 290 penetrates the lateral wall 292 of the sealed container 200 and the beverage liquid 202, reflects at the boundary between the beverage liquid 202 and the lateral wall 293 of the sealed container 200, penetrates the beverage liquid 202 and the lateral wall 292 of the sealed container 200 again, and returns back to the ultrasonic vibrator (as a sender sensor) 290. The above propagation time $t'_{293}$ is equal to $2 \times (t_{292} + t_{202})$.

Assuming that the diameter of the sealed container 200 is D, D is equal to $L_{292} + L_{202} + L_{293}$.

Generally, it can be assumed that $L_{292}$ is nearly equal to $L_{293}$.

Therefore, the sound velocity in the beverage liquid 202 can be evaluated according to the following formula.

$$V = \frac{D - 2 \cdot L_{292}}{\frac{t'_{290}}{2} - t_{292}} \qquad \text{Eq. 10'}$$

Since the liquid temperature t within the container and the sound velocity V can be evaluated from the foregoing Eq. 1 and the foregoing Eq. 10 or Eq. 10' respectively, the foregoing Eq. 6 is inversely calculated to evaluate the sugar content $\xi$ as in Eq. 9 above.

The press-contact means 240 is arranged so that it can advance and retract by means of a rectilinear reciprocating mechanism and, when it retracts, the lateral wall of the sealed container 200 is made to contact the ultrasonic vibrator 290. By detecting this timing, the ultrasonic vibrator 290 is oscillated with a single pulse by means of the ultrasonic shaker (pulse circuit) 425.

By this oscillating force, the pressure wave occurring within the beverage liquid 202 of the container 200 propagates through the beverage liquid 202 while the reflected wave is detected by the ultrasonic vibrator 290 to cause a voltage, which is detected by the amplifying wave detecting means 428 to be entered to the propagation time calculation means 429.

The propagation time calculation means 429 comprises a clock circuit 426 and a counter circuit 427, and opens the gate by the pulse trigger signal of the ultrasonic wave sender means 425 to start counting the clock pulse of the clock circuit 426, and closes the gate by the output of the amplifying wave detecting means 428 to end counting the clock pulse.

Assuming that the count value of the clock pulse is N and the clock frequency is f, then, according to $\tau = N/f$, the propagation time is calculated and outputted.

The propagation velocity V is calculated in the propagation velocity calculation means 430 according to Eq. 8.

(6) Calculation of the sugar content $\xi$:

The sugar content calculation means 431 calculates the sugar content $\xi$ according to the output V of the propagation velocity calculation means 430, the output t of the temperature characteristic calculation means 415 and Eq. 6 of the sugar content characteristic storage means 442.

From above, the gas density $\phi$ and the sugar content $\xi$ prevailing in the sealed container 200 are non-destructively and simultaneously measured.

(7) The measurement of the gas density $\phi$, sugar content $\xi$, time adjustment, display and recording of the container number, control of the movement and pressing force of the pressing means 210 and the control of the movement of the press-contact means 240 are carried out by the control means 400 partially including a computing function.

Next, the shaking apparatus intended for use with an apparatus for non-destructively inspecting the content of the container according to the fourth aspect of the present invention is described with reference to the four embodiments. First, a first embodiment is shown in FIG. 15.

This first embodiment is a shaking apparatus in which a can or a sealed container (hereinafter referred to as sealed container) 500 made of plastic material having an elastically deformable barrel portion is erected within a water tank 503 and the lower portion of the container 500 is immersed in the water of the water tank 503 for shaking.

A carbonated beverage is filled within the sealed container 500. This container 500 is erected in the water tank 503 filled with water, and the lower portion of the container 500 is submerged into the water. In addition, at the bottom portion of the water tank 503, an ultrasonic shaker 501 is mounted.

An ultrasonic power supply unit 502 for producing the alternating current of a frequency corresponding to the ultrasonic wave generated from the ultrasonic vibrator 501. The air actuator 504 is mounted on a fixed frame (corresponding to a hatched portion of the figure).

The air actuator 504 moves a pusher 507 to push the lateral surface of the container 500 in a horizontal direction. At the pusher 507, the mobile portion of an encoder 505 for detecting the displacement is mounted, and the sensor portion of the encoder 505 is mounted at the fixed frame.

The foregoing encoder 505 detects the distance over which the pusher is moved to send its displacement signal to a calculation unit 508. At the side opposite to the side where the pusher 507 for the container 500 strikes, a backing plate 509 having a recessed profile corresponding to the profile of the barrel portion of the container 500 is disposed. The backing plate 509 is mounted to the fixed frame with a load cell 506 positioned therebetween. The load cell 506 detects the force applied to the container 500 by the pusher 507 to send the detected signal to the calculation unit 508.

Next, the function of the apparatus shown in FIG. 15 is specifically described. The sealed container 500 filled with the carbonated beverage is set to a predetermined position of the water tank 503 filled with water. Thereafter, the ultrasonic vibrator 501 is energized by the alternating current of a predetermined frequency which has been converted by the ultrasonic power supply unit 502, so as to generate ultrasonic waves. The produced ultrasonic vibrations are transmitted to the sealed container 500 via water in the water tank 503 to shake the carbonated beverage inside the container 500.

While the carbonated beverage is being agitated for a certain period of time, it reaches an equilibrium condition between the gas and the liquid. When the gas-liquid equilibrium is reached, the generation of the ultrasonic wave is stopped, and the process is shifted to the inspection process.

In this first embodiment, the backing plate 509 is applied on the lateral surface of the container 500 to actuate the air actuator 504 to force the container 500 from the pusher 507 toward the backing plate. The displacement of the pusher 507 is detected by means of the encoder 505, and the resulting displacement signal is sent to the calculation unit 508. Further, the force with which the pusher 507 is pressed is detected by the load cell 506, and the resulting detection signal is sent to the calculation unit 508. The operating means of this unit 508 calculates the density of the dissolved carbonated gas within the carbonated beverage from both detection values.

Also, if one wants to make the liquid content uniform when he measures the sugar content in the container 500 or changes in the properties of the content, the ultrasonic shaker is set at the bottom portion of the water tank 503 and the content can be non-destructively inspected.

Figure 16:
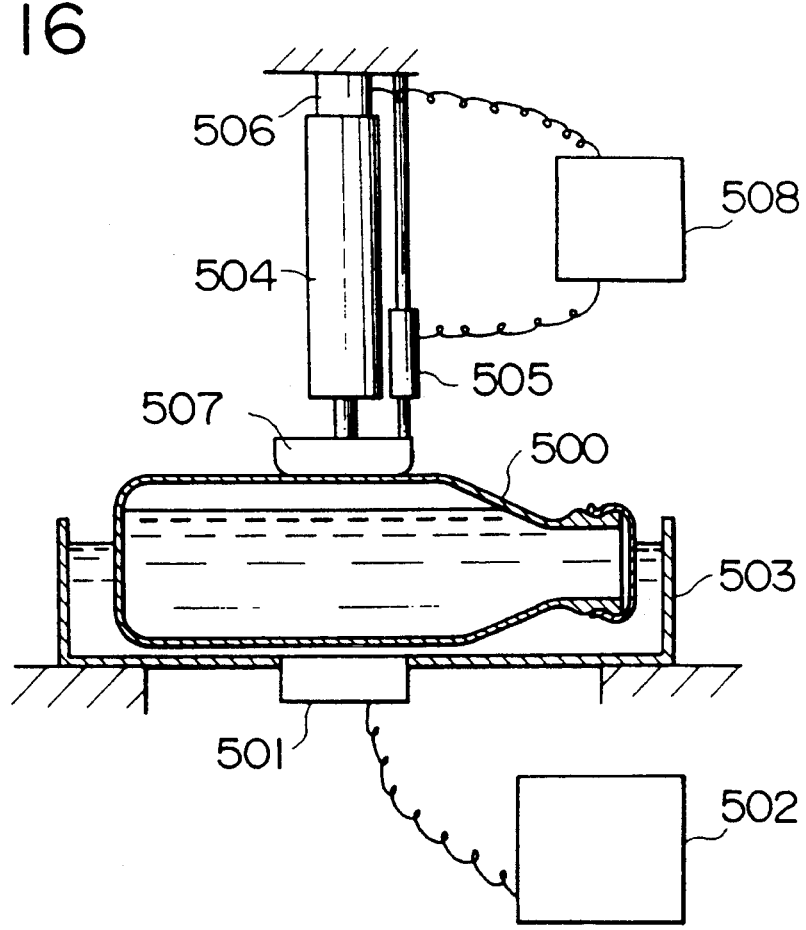
FIG. 16 is a schematic cross-sectional view illustrating a second embodiment of the shaking apparatus.

Next, FIG. 16 illustrates a second embodiment of the fourth aspect of the present invention. In this embodiment, the container 500 is turned over aside within the water tank 503 to immerse the lower lateral surface of container 500 into the water of the water tank 503 for shaking. With the container 500 lying sideways in the water tank 503, the lower lateral surface of the container 500 is submerged into the water. Therefore, in this embodiment, the backing plate 509 of the first embodiment is unnecessary, and with the upper lateral surface of the container forced against by the pusher 507, the lower lateral surface of the container 500 faces the bottom portion of the water tank 503.

The load cell 506 is interposed between the air actuator 504 and the fixed frame to detect the repulsive force. While the pusher 507 pushes the container 500, the load cell 506 detects a reaction force and sends the detection signal to the calculation unit 508.

In this second embodiment, since most of the container 500 is submerged in water, the weight of the container 500 per se becomes light under the buoyancy from water. The measuring accuracy is improved as compared with a case where no water is present because the container is less deformed by the weight of the container 500 itself.

Figure 17:
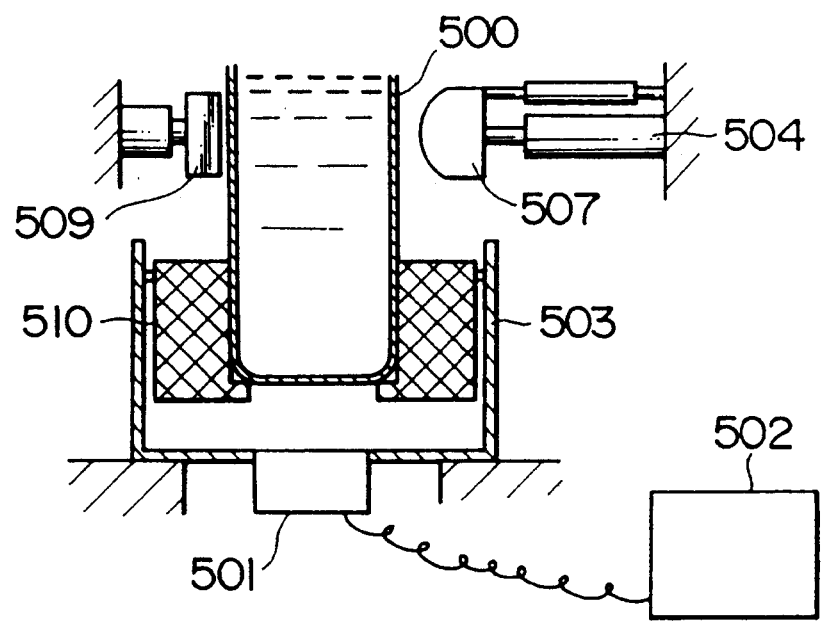
FIG. 17 is a schematical cross-sectional view illustrating a third embodiment of the shaking apparatus.
Figure 18:
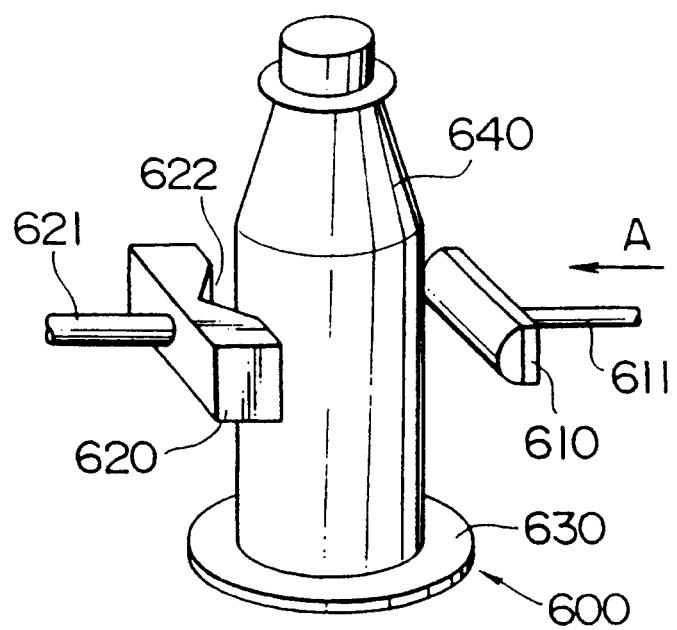
FIG. 18 is a schematic view illustrating a specific embodiment of an apparatus for positioning the container of the non-destructive apparatus according to the present invention.

Further, FIG. 17 illustrates a third embodiment according to the fourth aspect of the present invention. This third embodiment is a shaker in which, with the container 500 erected in the water tank 503 via a float 510, the lower portion of the container 500 is immersed in the water in the water tank 503 to shake the content of the container 500. The manner in which the container 500 is agitated by the container 500 is the same as in the first embodiment.

The float 510 exhibits a size with which a gap is formed between the same and the lateral wall of the water tank 503. When the internal pressure of the container 1 is measured and the container 500 is sandwiched by the pusher 507 and the backing plate 509, the container 500 completely floats on the water level, and the frictional force caused by the weight of the container 500 does not act at all. Thus the alignment can be made more easily by the container pinching members of the inspection apparatus, and measurements can be made even more accurate.

Incidentally, as modifications conceivable within the scope of this invention, there are the following. That is, according to the foregoing ultrasonic non-destructive inspection apparatus, a packaged container is placed on the measuring stand, and shifted to a predetermined position on the stand by means of the pressing member. The packaged container is sandwiched for fixation by the pressing member and the pedestal for positioning the container to start measuring. However, when the packaged container is shifted to the predetermined position on the measuring stand by the pressing member and positioned with the pressing member and the stand, it cannot frequently be smoothly moved to a predetermined position or cannot be positioned at a predetermined position, or can be abnormally deformed due to frictional resistances between the container and the measuring stand, between the container and the pedestal, and between the container and the pressing member.

In addition, in the foregoing apparatus, the position of the packaged container becomes unstable and its deformed condition can change, possibly resulting in a degraded measuring accuracy.

Accordingly, in order to solve those problems and improve the measuring accuracy, it is conceivable to add a container positioning apparatus.

This container positioning apparatus comprises a measuring rest for supporting the packaged container, a pedestal for positioning the container which pedestal is disposed in front in the direction in which the packaged container is moved on the measuring rest, and a pressing member for forcing the packaged container on the measuring stand toward the pedestal. In addition, on the measuring rest, a plurally of rails whose contact areas with the packaged container are small and which is made of a material having small frictional resistances relative to the packaged container are disposed in parallel to the direction in which the container travels.

This container positioning apparatus is arranged as follows. First, the packaged container is placed on the measuring rest, the pedestal and the pressing member is advanced. By forcing the packaged container in the direction of the pedestal and abutting it against the pedestal, the packaged container is positioned at a predetermined position on the measuring rest. At this time, the container receives frictional resistance from the measuring stand, the pedestal and the pressing member. However, since the foregoing rails are each provided on the measuring rest, the pedestal and the pressing member, even if the frictional resistance is extremely small and the pressing force of the pressing member is also small, the packaged container can be accurately positioned at the predetermined position on the measuring rest with a desired posture. Further, since the pressing force of the pressing member becomes small, the measuring accuracy is improved without causing an abnormal deformation to the packaged container.

Next, this positioning apparatus is described with reference to a specific embodiment shown in FIGS. 18 through 22. Reference numeral 600 denotes a positioning apparatus, 610 a pressing member, 620 a pedestal for positioning the container, 630 a measuring rest, and 640 a packaged container.

The foregoing packaged container 640 has a cylindrical cross-section, within which a beverage subjected to the non-destructive inspection is filled, and is placed the measuring rest 630.

Figure 22:
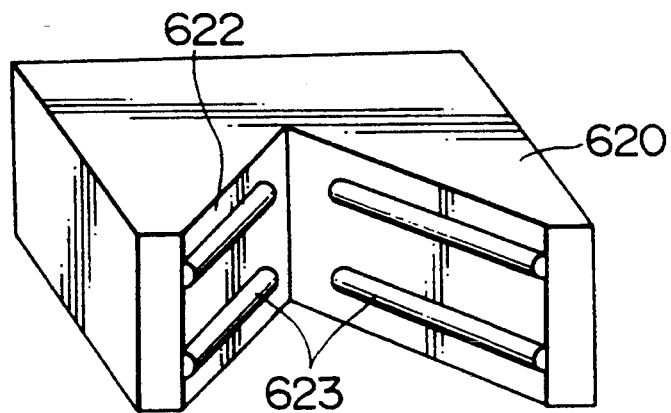
FIG. 22 is a perspective view illustrating a container positioning pedestal of the positioning apparatus of FIG. 18.
Figure 23:
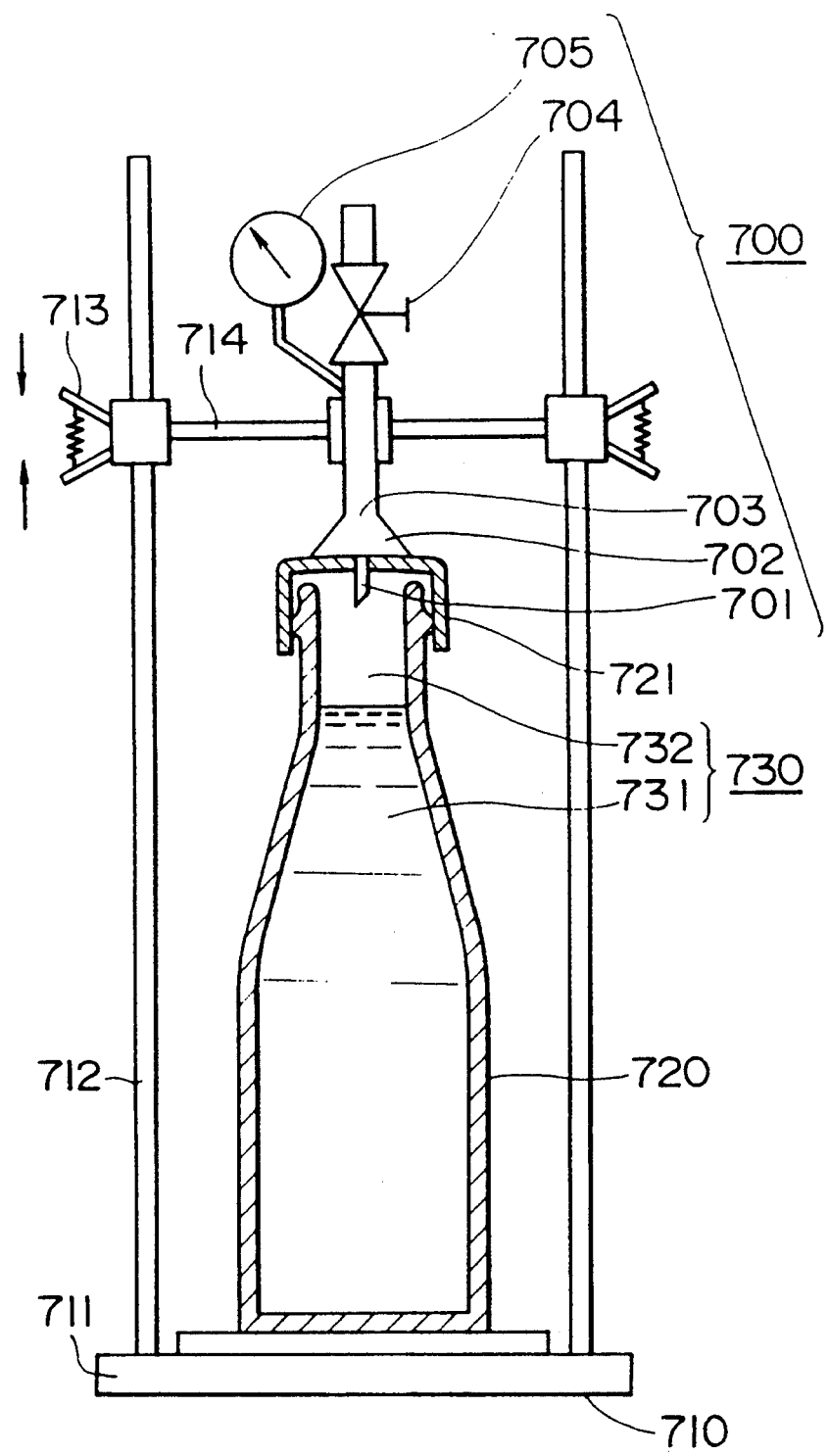
FIG. 23 is a schematic cross-sectional view illustrating a conventional density measuring apparatus.

The pedestal 620 for positioning the container is supported by the support member 621. The pedestal 620 has a triangular recess portion 622 on its front surface. If the ultrasonic sensor is necessary, it can be incorporated into this pedestal 620. Further, if the pressing force is necessary for measuring, then the load cell is incorporated between the support member 621 and the apparatus body. In addition, as shown in FIG. 22, on both sides of the triangular recess portion 622, two rails 623 of semicircular cross-section are each disposed side by side.

Figure 21:
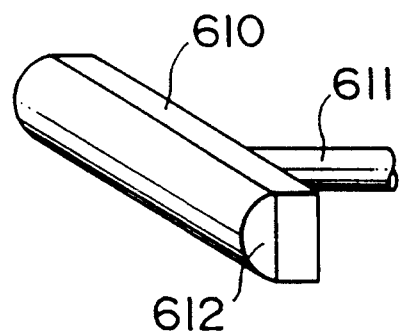
FIG. 21 is a perspective view illustrating a pressure member of the positioning apparatus.

The foregoing pressing member 610 is fixed to the apparatus body via a driving air cylinder (not shown) by means of a support rod 611 so as to advance in the direction of arrow A, but its rotational movement is restricted. Further, on the front surface of the pressing member 610, the rail 612 of semicircular cross-section is mounted, as shown in FIG. 21. This rail 612 is suitable for deforming the packaged container 640. When the ultrasonic shaker is provided, the upper and lower widths of the pressing member 610 of rectangular cross-section are widened, between which it is incorporated while, on the front surface of the pressing member 610, two rails 612 of semicircular cross-section may be provided side by side.

Figure 19:
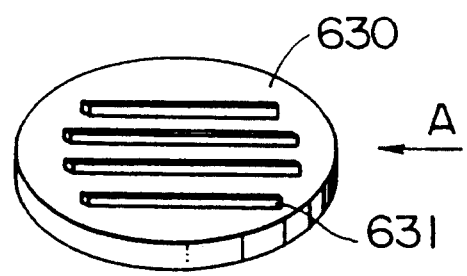
FIG. 19 is a perspective view illustrating a measuring stand for the positioning apparatus of FIG. 18.
Figure 20:
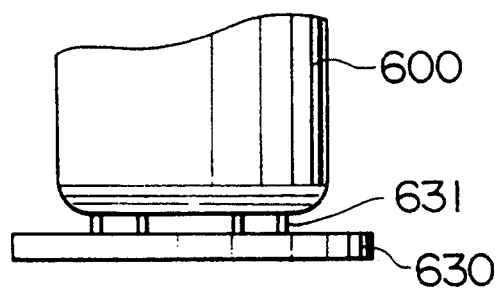
FIG. 20 is a partial elevational view illustrating the measuring stand of the positioning apparatus of FIG. 18.

As shown in FIGS. 19 and 20, on the measuring stand 630, a plurality (four in FIG. 19) of rails 631 small in contact area with the container 640 and also small in frictional resistance against the container 640 (for example, tetrafluoride resin) is each disposed in parallel to the direction in which the container 640 travels.

Incidentally, the foregoing rails 612 and 623 as well as the rail 631 are made of a material whose area contacting the packaged container 640 is small and whose frictional resistance against the same is small (for example, tetrafluoride resin).

Next, the operation of this positioning apparatus is specifically described. First, the packaged container 640 is placed on each rail 631 of the measuring rest 630, and subsequently the pressing member 610 is advanced in the direction of arrow A to force the packaged container 640 in the direction of the pedestal 620 to abut either one of the lateral surfaces of the triangular recess portion 622 of the pedestal 620.

Since the triangular pedestal 622 is inclined at a predetermined angle (for example, about 45 degrees) relative to the traveling direction (arrow A) of the packaged container 640, the packaged container 640, traveling in the direction of arrow A, also travels in the lateral direction toward the other lateral surface, and abuts both lateral surfaces of the triangular recess portion 622 and stops.

Meanwhile, the packaged container 640 receives the frictional resistance from the measuring rest 630, the pedestal 620 and pressing member 610. However, since the rails 631, 623, 612 made of the foregoing material (for example, tetrafluoride resin) are each provided at the measuring rest 630, pedestal 620 and pressing member 610, even if the frictional resistance is extremely small and the pressing force of the pressing member 610 is small, the packaged container 640 can be accurately positioned at the predetermined position without collapsing its erected position. In addition, since the pressing force of the pressing member 610 is small, no abnormal deformation occurs to the packaged container 640.

As described above, with this positioning apparatus, the packaged container is placed on the measuring rest, and subsequently the pressing member is advanced to force the packaged container toward the pedestal for abutment to position to the predetermined position on the measuring rest. At this time, the packaged container receives the frictional resistance from the measuring rest, the pedestal and the pressing member. However, since the rails made of a material whose areas contacting the packaged container are small and whose frictional resistance against the same is small are each provided at the measuring stand, pedestal and the pressing member, the frictional resistance can be extremely made small. Further, even if the pressing force of the pressing member is small, the packaged container can be accurately positioned at the predetermined position with a desired posture. Still further, since the pressing force of the pressing member may be small, the measuring accuracy can be improved without causing an abnormal deformation to the packaged container.

What is claimed is:

1. An apparatus for measuring gas density of a liquid beverage in an interior of a sealed container under an internal pressure P comprising:

pressing means for pressing a lateral surface of a sealed container containing a beverage with a variable load F;

displacement measuring means for measuring displacement X of said pressing means when said sealed container is elastically deformed by said pressing means to vary said internal pressure P in said container;

load measuring means for measuring said load F applied by said pressing means;

container rigidity first calculation means for calculating container rigidity $((\delta F/\delta X)_{p=p})$ in terms of said internal pressure P in response to measurements by said displacement measuring means and said load measuring means;

non-destructive internal pressure measuring means for non-destructively measuring said pressure P in said container in response to said rigidity calculated by said first calculation means by determining the gradient characteristic $(P=f(\delta F/\delta X)_p$ based on said calculated container rigidity $((\delta F/\delta X)_{p=p})$ in terms of said pressure P;

surface temperature measuring means for measuring surface temperature T of said container; and solubility characteristic $\phi$ (P, T) second calculation means for calculating solubility $\phi$ of gas in said beverage based on said pressure measured by said pressure measuring means, said surface temperature T measured by said surface temperature measuring means, and said solubility characteristic $\phi(P, T)$ determined depending on the gas and beverage liquid in said container.

2. The apparatus for measuring gas density of a beverage within a sealed container as claimed in claim 1 and further comprising:

a water tank containing water for immersing a part of said sealed container in said water; and a shaker for transmitting an ultrasonic vibration from a lower portion of said water tank to said interior of said sealed container through said water.

3. The apparatus for measuring gas density of a beverage in a sealed container as claimed in claim 1 wherein said water has an upper surface level in said tank and further comprising:

a float in said tank engageable with said container for supporting said container partly immersed in said water at a predetermined position relative to said surface level of said water.

4. A method of measuring gas density of a liquid beverage within a sealed container under an internal pressure P comprising:

pressing a lateral surface of a sealed container containing a beverage with a variable load F by a pressing means to elastically deform said sealed container to vary said pressure P in said sealed container;

measuring displacement of said pressing means by a displacement measuring means, while simultaneously measuring said load F applied to said pressing means by a load measuring means;

transmitting said measured displacement and load to a container rigidity calculation means and calculating rigidity of said container $((\delta F/\delta X)_{p=p})$ in terms of said internal pressure P;

transmitting said calculated rigidity to a non-destructive internal pressure measuring means and determining said internal pressure P non-destructively by determining a gradient characteristic $(P=f(\delta F/\delta X)_p)$ based on said calculated container rigidity $((\delta F/\delta X)_{p=p})$ in terms of said internal pressure P;

measuring surface temperature T of said container;

transmitting said measured internal pressure, said surface temperature T, and a solubility characteristic $\phi(P, T)$ depending on the gas and beverage liquid in said container to a solubility characteristic calculation means; and calculating solubility $\phi$ of said gas in said beverage liquid.

5. An apparatus for measuring sugar content of a beverage in an interior of a sealed container comprising:

calculation control means for emitting a measurement start signal and for calculating beverage temperature;

a pulser for converting said measurement start signal into a high voltage pulse;

an ultrasonic wave sensor having a wave sender portion for converting said high voltage pulse from said pulser into a pressure wave of an ultrasonic frequency and radiating said pressure wave into a beverage in a sealed container, and a wave receiver portion for receiving said pressure wave and emitting an output signal;

an amplifier for amplifying said output signal from said wave receiver portion and emitting an output signal;

a comparator for comparing said output signal from said amplifier with a preset value and emitting an output signal;

an ultrasonic timing means for starting to time with said measurement start signal and ending timing with said output signal from said comparator and emitting a timing signal;

a container surface temperature sensor for measuring surface temperature of said sealed container and emitting a signal indicative thereof;

an ambient temperature sensor for measuring ambient temperature proximate said sealed container and emitting a signal indicative thereof;

pressure-contact means for pressing said ultrasonic wave sensor and said container surface temperature sensor into contact with said sealed container;

said calculation control means, after said ultrasonic sensor and said container surface temperature sensor are pressed into contact with said sealed container, calculating beverage temperature within said sealed container based on said surface temperature measurement signal and said ambient temperature measurement signal from said temperature sensors, respectively, while calculating propagation velocity of said pressure wave based on said timing signal from said ultrasonic timing means and propagation distance of said pressure wave, and further calculating sugar content of said beverage based on said calculated propagation velocity and said calculated beverage temperature; and sugar content display means for displaying or recording a result calculated by said calculation control means.

6. The apparatus for measuring gas density of a beverage within a sealed container as claimed in claim 5 and further comprising:

a water tank containing water for immersing a part of said sealed container in said water; and a shaker for transmitting an ultrasonic vibration from a lower portion of said water tank to said interior of said sealed container through said water.

7. The apparatus for measuring gas density of a beverage in a sealed container as claimed in claim 6 wherein said water has an upper surface level in said tank and further comprising:

a float in said tank engageable with said container for supporting said container partly immersed in said water at a predetermined position relative to said surface level of said water.

8. A method of measuring sugar content of a beverage within a sealed container comprising:

pressing an ultrasonic sensor and a container surface temperature sensor into contact with a sealed container containing a beverage therein by a press-contact means;

converting a measurement start signal pulse from a calculation control means into a high voltage pulse by a pulser means;

converting said high voltage pulse into a pressure wave of an ultrasonic frequency by a wave sender portion of said ultrasonic sensor and radiating said pressure wave into said beverage;

receiving said pressure wave by a wave receiver portion of said ultrasonic wave sensor and emitting an output signal therefrom;

amplifying said output signal from said wave receiver portion by an amplifier means and comparing said output signal from said wave receiver portion with a preset value by a comparator means;

emitting an output signal from said comparator;

starting to time with said measurement start signal pulse by an ultrasonic timing means and ending timing with said output signal from said comparator;

emitting a timing signal from said timing means;

measuring surface temperature of said sealed container by said container surface temperature sensor and emitting an output signal indicative thereof;

measuring ambient temperature proximate said sealed container by an ambient temperature sensor and emitting an output signal indicative thereof;

calculating the temperature of said beverage based on said output signal from said container surface temperature sensor and said output signal from said ambient temperature sensor;

calculating propagation velocity of said pressure wave based on said timing signal from said ultrasonic timing means and propagation distance of said pressure wave within said beverage;

calculating sugar content of said beverage according to said propagation velocity and said calculated beverage temperature; and displaying or recording results by a sugar content display means.

9. An apparatus for simultaneously measuring sugar content $\xi$ and gas density $\phi$ of a beverage under internal pressure P in an interior of a sealed container comprising:

means for measuring gas density of a beverage in a sealed container;

means for measuring sugar content of said beverage;

movable pressing means for producing a pressure force F on said container;

movable press-contact means; and control means for recording or displaying measured values of said gas density, said sugar content, time adjustment, and a container number, and for controlling movement and said pressing force F of said pressing means and movement of said press-contact means;

said gas density measuring means comprising a box-shaped container stand for holding said sealed container filled with a beverage liquid and a gas under internal pressure P, surface temperature detecting means for detecting surface temperature $t_w$ of said sealed container, ambient temperature detecting means for detecting ambient temperature $t_a$, load measuring means fixed to a part of said container stand, said pressing means being engageable with said container for forcing said container against said load measuring means, displacement measuring means for measuring displacement X of said pressing means, container rigidity calculation means for calculating container rigidity $k_p = (\delta F / \delta X)_p$ based on said pressing force F and said displacement X, temperature characteristic storage means for storing a relationship $t = t(t_w, t_a)$ between said container, container rigidity characteristic storage means for storing a relationship $P = P(k_p)$ between said internal pressure P and said container rigidity $k_p$, gas-liquid equilibrium characteristic storage means for storing gas-liquid equilibrium density characteristic $\phi(P, t)$ determined based on said beverage liquid, said internal pressure P and said liquid temperature t, temperature characteristic calculation means for calculating said liquid temperature t based on said relationship $t = t(t_w, t_a)$, and gas-liquid equilibrium density calculation means for calculating said internal pressure P from said container rigidity $k_p$ and calculating and outputting gas density $\phi$ of said beverage liquid with which said gas is in a gas-liquid equilibrium state from said internal pressure, said liquid temperature t and said gas-liquid equilibrium characteristic $\phi(P, t)$;

said sugar content measuring means comprising at least one ultrasonic vibrator mounted on said container stand, said press-contact means being engageable with said container for forcing said container against said ultrasonic vibrator, ultrasonic shaker means operatively connected to said ultrasonic vibrator for driving said ultrasonic vibrator with a single pulse, said ultrasonic vibrator being energized by said ultrasonic shaker means for inducing an ultrasonic elastic wave in said sealed container, ultrasonic wave detecting means for amplifying an electrical output from said ultrasonic vibrator and detecting an envelope thereof, a propagation velocity calculation means for calculating propagation velocity V of said ultrasonic wave in said beverage liquid based on outputs from said ultrasonic shaker means and said ultrasonic wave detecting means, sound velocity characteristic storage means for storing a relationship $V=v(t, \xi)$ between said propagation velocity V, said liquid temperature t and said sugar content $\xi$, and sugar content calculation means for calculating said sugar content $\xi$ from said propagation velocity V, said liquid temperature t and said relationship $V=v(t, \xi)$.

10. The apparatus for measuring gas density of a beverage within a sealed container as claimed in claim 9 and further comprising:
- a water tank containing water for immersing a part of said sealed container in said water; and
- a shaker for transmitting an ultrasonic vibration from a lower portion of said water tank to said interior of said sealed container through said water.

11. The apparatus for measuring gas density of a beverage in a sealed container as claimed in claim 10 wherein said water has an upper surface level in said tank and further comprising:
- a float in said tank engageable with said container for supporting said container partly immersed in said water at a predetermined position relative to said surface level of said water.

12. The apparatus for simultaneously measuring the sugar content $\xi$ and gas density $\phi$ of a beverage within a sealed container as claimed in claim 9, wherein:
- said sugar content measuring means further comprises a pair of ultrasonic vibrators;
- said press-contact means presses said sealed container in at least two opposite positions thereon against said pair of ultrasonic vibrators;
- said ultrasonic shaker means drives at least one of said ultrasonic vibrators with a single pulse, at least one of said ultrasonic vibrators being energized by said ultrasonic shaker means for inducing an ultrasonic elastic wave in said sealed container; and
- said ultrasonic wave detecting means amplifies an electrical output from at least one of said ultrasonic vibrators and detects an envelope thereof.

13. The apparatus for measuring gas density of a beverage within a sealed container as claimed in claim 12 and further comprising:
- a water tank containing water for immersing a part of said sealed container in said water; and
- a shaker for transmitting an ultrasonic vibration from a lower portion of said water tank to said interior of said sealed container through said water.

14. The apparatus for measuring gas density of a beverage in a sealed container as claimed in claim 13 wherein said water has an upper surface level in said tank and further comprising:
- a float in said tank engageable with said container for supporting said container partly immersed in said water at a predetermined position relative to said surface level of said water.

15. A method of simultaneously measuring sugar content and gas density of a beverage within a sealed container comprising:

placing upright a sealed container filled with a beverage liquid and a gas under internal pressure P on a container stand having a box shape;

detecting surface temperature $t_w$ of said sealed container by a surface temperature detecting means;

detecting ambient temperature $t_a$ proximate said sealed container by an ambient temperature detecting means;

forcing said sealed container against a load measuring means fixed to a part of said container stand by a force F of a pressing means;

measuring displacement X of said pressing means by a displacement measuring means;

calculating container rigidity $k_p=(\delta F/\delta X)_p$ from said pressing force F and displacement X by a container rigidity calculation means;

calculating liquid temperature t in said container from the relationship $t=(t_w, t_a)$ between said container surface temperature $t_w$, said ambient temperature $t_a$ and said liquid temperature t by a temperature characteristic calculation means;

calculating said internal pressure P based on a relationship $P=P(k_p)$ between said internal pressure P and said container rigidity $k_p$ by said container rigidity calculation means:

calculating gas density in said beverage liquid at which said liquid and gas are in an equilibrium state from said calculated internal pressure P and said gas-liquid equilibrium characteristic $\phi=\phi(P, t)$ determined according to said beverage liquid, said internal pressure P and said liquid temperature t;

pressing said sealed container against an ultrasonic vibrator by a press-contact means;

driving said ultrasonic vibrator with a single pulse produced by an ultrasonic shaker means to induce an ultrasonic elastic wave in said sealed container;

amplifying an electrical output from said ultrasonic vibrator and detecting an envelope thereof by ultrasonic wave detecting means;

calculating propagation velocity V of said ultrasonic wave in said beverage liquid from outputs from said ultrasonic shaker means and said ultrasonic wave detector by a propagation velocity calculation means; and calculating sugar content $\xi$ from a relationship $V=v(t, \xi)$ between said ultrasonic wave propagation velocity V, said liquid temperature t and said sugar content $\xi$ by a sugar content calculation means.

16. The method of simultaneously measuring sugar content and gas density of a beverage within a sealed container as claimed in claim 15 wherein:
- a pair of ultrasonic vibrators are used and said sealed container is pressed at two opposite positions thereon by said press-contact means against said pair of vibrators;
- at least one of said ultrasonic vibrators is driven by a single pulse from said ultrasonic shaker means to induce said ultrasonic elastic wave in said sealed container; and
- an electrical output from at least one of said ultrasonic vibrators is amplified to detect an envelope thereof.

17. A shaking apparatus used with an apparatus for non-destructively inspecting contents in a sealed container, said contents containing a water-soluble gas and said sealed container having an elastically deformable barrel portion, said shaking apparatus agitating said contents prior to inspecting internal pressure in said container and sugar content thereof and comprising:
 a water tank for immersing a part of said container to be inspected in water therein, and an ultrasonic vibrator operatively connected to said tank for transmitting ultrasonic vibrations from a lower portion of said water tank through said water to the interior of said container.

18. The shaking apparatus as claimed in claim 17 wherein said water has an upper surface level in said tank and further comprising:
 a float in said water tank engageable with said container for supporting said container partly immersed in said water at a predetermined position relative to said surface level of said water.

* * * * *